(12) United States Patent
Huang

(10) Patent No.: US 7,193,053 B2
(45) Date of Patent: Mar. 20, 2007

(54) HYPOXIA-INDUCIBLE FACTOR 1ALPHA VARIANTS AND METHODS OF USE

(75) Inventor: L. Eric Huang, Germantown, MD (US)

(73) Assignee: United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 10/831,380

(22) Filed: Apr. 23, 2004

(65) Prior Publication Data

US 2005/0202450 A1 Sep. 15, 2005

Related U.S. Application Data

(60) Provisional application No. 60/465,565, filed on Apr. 25, 2003.

(51) Int. Cl.
*A61K 14/00* (2006.01)
(52) U.S. Cl. .................................................. 530/350
(58) Field of Classification Search ................ 530/350
See application file for complete search history.

(56) References Cited

U.S. PATENT DOCUMENTS

2002/0048794 A1* 4/2002 Poellinger et al. ......... 435/69.1

2003/0045686 A1* 3/2003 Kaelin et al. ............... 530/350

OTHER PUBLICATIONS

Huang et al., "Leu-574 of HIF-1-alpha is Essential for the von Hippel-Lindau (VHL)-mediated Degradation Pathway", The Journal of Biological Chemistry. Nov. 1, 2002. vol. 277, No. 44, pp. 41750-41755.*
Masson et al., "Independent Function of Two Destruction Domains of Hypoxia-Inducible Factor-alpha Chains Activated by Prolyl Hydroxylation". The EMBO Journal. 2001. vol. 20, No. 18, pp. 5197-5206.*
Huang et al. Regulation of Hypoxia-Inducible Factor 1-alpha is Mediated by an Oxygen-dependent Degradation Domain Via the Ubiquitin-Proteasome Pathway. Proceedings of the National Academies of Science. Jul. 1998. Vo. 95, pp. 7987-7992.*

* cited by examiner

*Primary Examiner*—Karen Cochrane Carlson
*Assistant Examiner*—Suzanne M. Noakes
(74) *Attorney, Agent, or Firm*—Peter F. Corless, Esq.; Gregory B. Butler, Esq.; Edwards Angell Palmer & Dodge, LLP

(57) ABSTRACT

This invention relates to unique variant forms of HIF-1 alpha polypeptide that are stable under hypoxic and nonhypoxic conditions and their use in the treatment of disorders involving oxygen homeostasis.

17 Claims, 14 Drawing Sheets

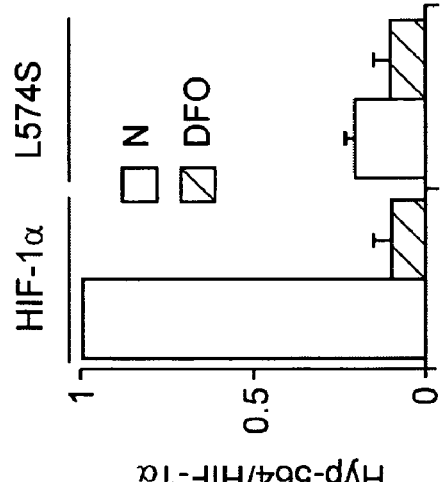
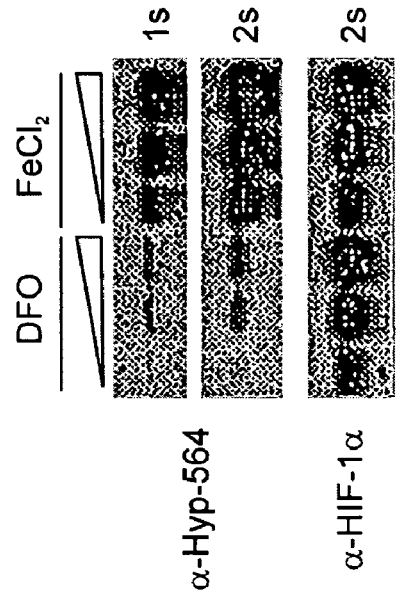
FIG. 7B
FIG. 7A
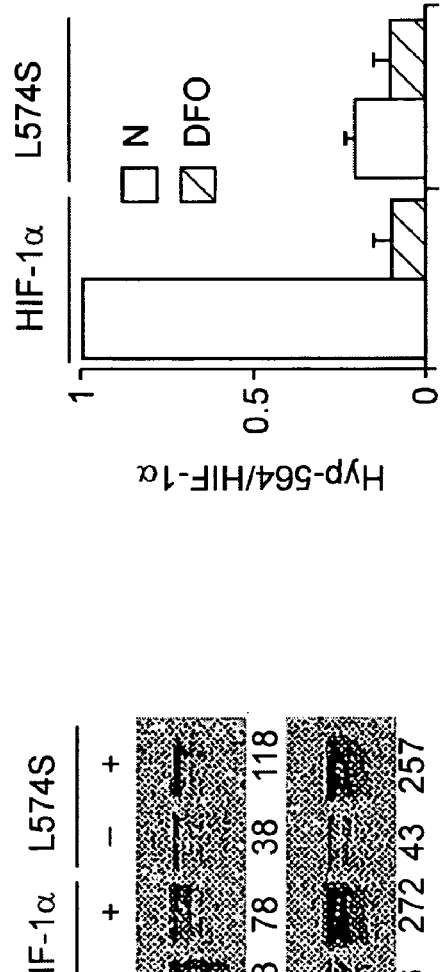
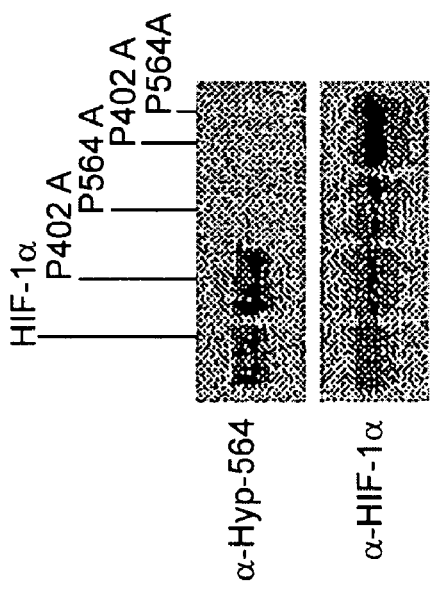
FIG. 7D
FIG. 7C

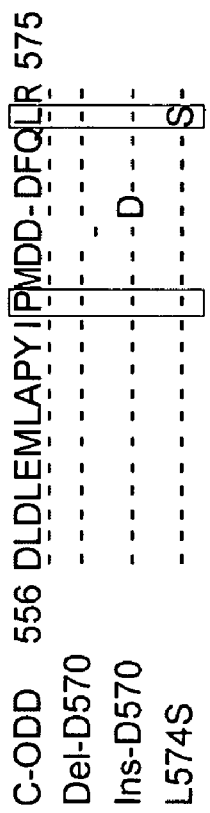
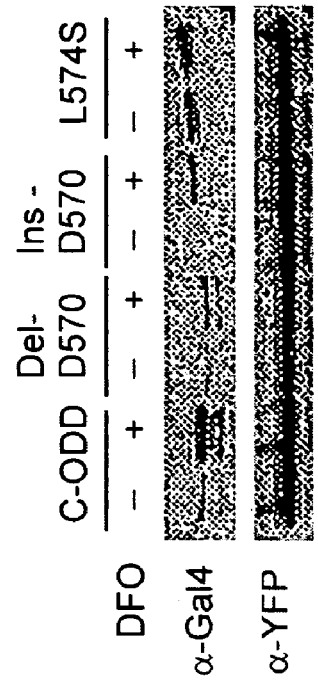
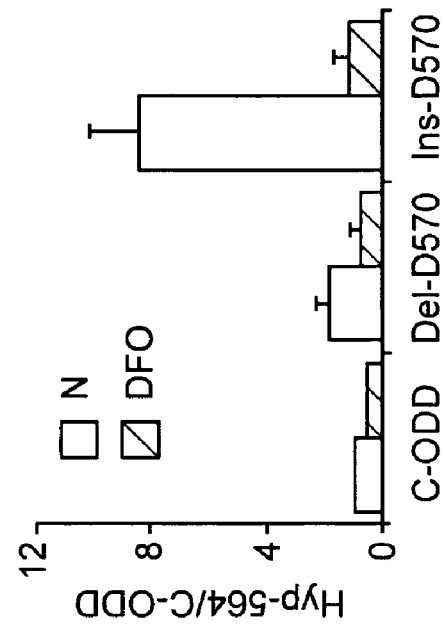
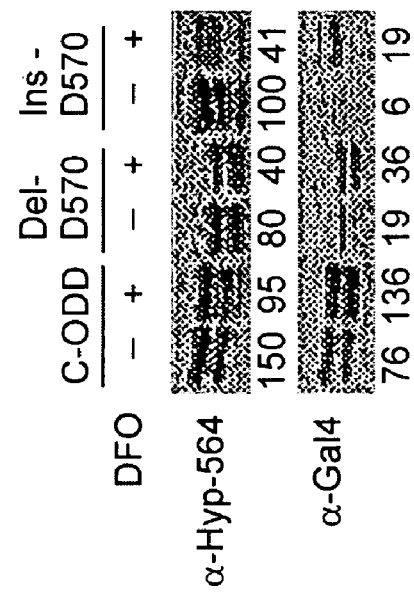
FIG. 9A
FIG. 9B
FIG. 9C
FIG. 9D

SEQUENCE LISTING

<160> NUMBER OF SEQ ID NOS: 2

<210> SEQ ID NO 1
<211> LENGTH: 3736
<212> TYPE: DNA
<213> ORGANISM: Homo sapiens
<220> FEATURE:
<221> NAME/KEY: CDS
<222> LOCATION: (29)..(2506)

<400> SEQUENCE: 1

```
gtgaagacat cgcggggacc gattcacc atg gag ggc gcc ggc ggc gcg aac         52
                                Met Glu Gly Ala Gly Gly Ala Asn
                                  1               5 gac aag aaa aag ata agt tct gaa cgt cga aaa gaa aag tct cga gat       100
Asp Lys Lys Lys Ile Ser Ser Glu Arg Arg Lys Glu Lys Ser Arg Asp
 10              15                  20 gca gcc aga tct cgg cga agt aaa gaa tct gaa gtt ttt tat gag ctt       148
Ala Ala Arg Ser Arg Arg Ser Lys Glu Ser Glu Val Phe Tyr Glu Leu
 25              30                  35                  40 gct cat cag ttg cca ctt cca cat aat gtg agt tcg cat ctt gat aag       196
Ala His Gln Leu Pro Leu Pro His Asn Val Ser Ser His Leu Asp Lys
             45                  50                  55 gcc tct gtg atg agg ctt acc atc agc tat ttg cgt gtg agg aaa ctt       244
Ala Ser Val Met Arg Leu Thr Ile Ser Tyr Leu Arg Val Arg Lys Leu
         60                  65                  70 ctg gat gct ggt gat ttg gat att gaa gat gac atg aaa gca cag atg       292
Leu Asp Ala Gly Asp Leu Asp Ile Glu Asp Asp Met Lys Ala Gln Met
     75                  80                  85 aat tgc ttt tat ttg aaa gcc ttg gat ggt ttt gtt atg gtt ctc aca       340
Asn Cys Phe Tyr Leu Lys Ala Leu Asp Gly Phe Val Met Val Leu Thr
 90                  95                 100 gat gat ggt gac atg att tac att tct gat aat gtg aac aaa tac atg       388
Asp Asp Gly Asp Met Ile Tyr Ile Ser Asp Asn Val Asn Lys Tyr Met
105                 110                 115                 120 gga tta act cag ttt gaa cta act gga cac agt gtg ttt gat ttt act       436
Gly Leu Thr Gln Phe Glu Leu Thr Gly His Ser Val Phe Asp Phe Thr
```

-continued

|  |  |  |  |  |  |  |  |  |  |  |  |  |  |  |  |
|---|---|---|---|---|---|---|---|---|---|---|---|---|---|---|---|
|  |  | 125 |  |  |  | 130 |  |  |  |  | 135 |  |  |  |  |

```
cat cca tgt gac cat gag gaa atg aga gaa atg ctt aca cac aga aat      484
His Pro Cys Asp His Glu Glu Met Arg Glu Met Leu Thr His Arg Asn
            140                 145                 150 ggc ctt gtg aaa aag ggt aaa gaa caa aac aca cag cga agc ttt ttt      532
Gly Leu Val Lys Lys Gly Lys Glu Gln Asn Thr Gln Arg Ser Phe Phe
        155                 160                 165 ctc aga atg aag tgt acc cta act agc cga gga aga act atg aac ata      580
Leu Arg Met Lys Cys Thr Leu Thr Ser Arg Gly Arg Thr Met Asn Ile
        170                 175                 180 aag tct gca aca tgg aag gta ttg cac tgc aca ggc cac att cac gta      628
Lys Ser Ala Thr Trp Lys Val Leu His Cys Thr Gly His Ile His Val
185                 190                 195                 200 tat gat acc aac agt aac caa cct cag tgt ggg tat aag aaa cca cct      676
Tyr Asp Thr Asn Ser Asn Gln Pro Gln Cys Gly Tyr Lys Lys Pro Pro
                205                 210                 215 atg acc tgc ttg gtg ctg att tgt gaa ccc att cct cac cca tca aat      724
Met Thr Cys Leu Val Leu Ile Cys Glu Pro Ile Pro His Pro Ser Asn
            220                 225                 230 att gaa att cct tta gat agc aag act ttc ctc agt cga cac agc ctg      772
Ile Glu Ile Pro Leu Asp Ser Lys Thr Phe Leu Ser Arg His Ser Leu
        235                 240                 245 gat atg aaa ttt tct tat tgt gat gaa aga att acc gaa ttg atg gga      820
Asp Met Lys Phe Ser Tyr Cys Asp Glu Arg Ile Thr Glu Leu Met Gly
        250                 255                 260 tat gag cca gaa gaa ctt tta ggc cgc tca att tat gaa tat tat cat      868
Tyr Glu Pro Glu Glu Leu Leu Gly Arg Ser Ile Tyr Glu Tyr Tyr His
265                 270                 275                 280 gct ttg gac tct gat cat ctg acc aaa act cat cat gat atg ttt act      916
Ala Leu Asp Ser Asp His Leu Thr Lys Thr His His Asp Met Phe Thr
                285                 290                 295 aaa gga caa gtc acc aca gga cag tac agg atg ctt gcc aaa aga ggt      964
Lys Gly Gln Val Thr Thr Gly Gln Tyr Arg Met Leu Ala Lys Arg Gly
            300                 305                 310 gga tat gtc tgg gtt gaa act caa gca act gtc ata tat aac acc aag     1012
Gly Tyr Val Trp Val Glu Thr Gln Ala Thr Val Ile Tyr Asn Thr Lys
        315                 320                 325 aat tct caa cca cag tgc att gta tgt gtg aat tac gtt gtg agt ggt     1060
Asn Ser Gln Pro Gln Cys Ile Val Cys Val Asn Tyr Val Val Ser Gly
        330                 335                 340 att att cag cac gac ttg att ttc tcc ctt caa caa aca gaa tgt gtc     1108
Ile Ile Gln His Asp Leu Ile Phe Ser Leu Gln Gln Thr Glu Cys Val
345                 350                 355                 360 ctt aaa ccg gtt gaa tct tca gat atg aaa atg act cag cta ttc acc     1156
Leu Lys Pro Val Glu Ser Ser Asp Met Lys Met Thr Gln Leu Phe Thr
                365                 370                 375 aaa gtt gaa tca gaa gat aca agt agc ctc ttt gac aaa ctt aag aag     1204
Lys Val Glu Ser Glu Asp Thr Ser Ser Leu Phe Asp Lys Leu Lys Lys
            380                 385                 390 gaa cct gat gct tta act ttg ctg gcc cca gcc gct gga gac aca atc     1252
Glu Pro Asp Ala Leu Thr Leu Leu Ala Pro Ala Ala Gly Asp Thr Ile
        395                 400                 405 ata tct tta gat ttt ggc agc aac gac aca gaa act gat gac cag caa     1300
Ile Ser Leu Asp Phe Gly Ser Asn Asp Thr Glu Thr Asp Asp Gln Gln
        410                 415                 420 ctt gag gaa gta cca tta tat aat gat gta atg ctc ccc tca ccc aac     1348
Leu Glu Glu Val Pro Leu Tyr Asn Asp Val Met Leu Pro Ser Pro Asn
425                 430                 435                 440 gaa aaa tta cag aat ata aat ttg gca atg tct cca tta ccc acc gct     1396
```

-continued

| | | |
|---|---|---|
| Glu Lys Leu Gln Asn Ile Asn Leu Ala Met Ser Pro Leu Pro Thr Ala<br>445              450              455 | | |
| gaa acg cca aag cca ctt cga agt agt gct gac cct gca ctc aat caa<br>Glu Thr Pro Lys Pro Leu Arg Ser Ser Ala Asp Pro Ala Leu Asn Gln<br>460              465              470 | 1444 | |
| gaa gtt gca tta aaa tta gaa cca aat cca gag tca ctg gaa ctt tct<br>Glu Val Ala Leu Lys Leu Glu Pro Asn Pro Glu Ser Leu Glu Leu Ser<br>475              480              485 | 1492 | |
| ttt acc atg ccc cag att cag gat cag aca cct agt cct tcc gat gga<br>Phe Thr Met Pro Gln Ile Gln Asp Gln Thr Pro Ser Pro Ser Asp Gly<br>490              495              500 | 1540 | |
| agc act aga caa agt tca cct gag cct aat agt ccc agt gaa tat tgt<br>Ser Thr Arg Gln Ser Ser Pro Glu Pro Asn Ser Pro Ser Glu Tyr Cys<br>505              510              515              520 | 1588 | |
| ttt tat gtg gat agt gat atg gtc aat gaa ttc aag ttg gaa ttg gta<br>Phe Tyr Val Asp Ser Asp Met Val Asn Glu Phe Lys Leu Glu Leu Val<br>525              530              535 | 1636 | |
| gaa aaa ctt ttt gct gaa gac aca gaa gca aag aac cca ttt tct act<br>Glu Lys Leu Phe Ala Glu Asp Thr Glu Ala Lys Asn Pro Phe Ser Thr<br>540              545              550 | 1684 | |
| cag gac aca gat tta gac ttg gag atg tta gct ccc tat atc cca atg<br>Gln Asp Thr Asp Leu Asp Leu Glu Met Leu Ala Pro Tyr Ile Pro Met<br>555              560              565 | 1732 | |
| gat gat gac ttc cag tta cgt tcc ttc gat cag ttg tca cca tta gaa<br>Asp Asp Asp Phe Gln Leu Arg Ser Phe Asp Gln Leu Ser Pro Leu Glu<br>570              575              580 | 1780 | |
| agc agt tcc gca agc cct gaa agc gca agt cct caa agc aca gtt aca<br>Ser Ser Ser Ala Ser Pro Glu Ser Ala Ser Pro Gln Ser Thr Val Thr<br>585              590              595              600 | 1828 | |
| gta ttc cag cag act caa ata caa gaa cct act gct aat gcc acc act<br>Val Phe Gln Gln Thr Gln Ile Gln Glu Pro Thr Ala Asn Ala Thr Thr<br>605              610              615 | 1876 | |
| acc act gcc acc act gat gaa tta aaa aca gtg aca aaa gac cgt atg<br>Thr Thr Ala Thr Thr Asp Glu Leu Lys Thr Val Thr Lys Asp Arg Met<br>620              625              630 | 1924 | |
| gaa gac att aaa ata ttg att gca tct cca tct cct acc cac ata cat<br>Glu Asp Ile Lys Ile Leu Ile Ala Ser Pro Ser Pro Thr His Ile His<br>635              640              645 | 1972 | |
| aaa gaa act act agt gcc aca tca tca cca tat aga gat act caa agt<br>Lys Glu Thr Thr Ser Ala Thr Ser Ser Pro Tyr Arg Asp Thr Gln Ser<br>650              655              660 | 2020 | |
| cgg aca gcc tca cca aac aga gca gga aaa gga gtc ata gaa cag aca<br>Arg Thr Ala Ser Pro Asn Arg Ala Gly Lys Gly Val Ile Glu Gln Thr<br>665              670              675              680 | 2068 | |
| gaa aaa tct cat cca aga agc cct aac gtg tta tct gtc gct ttg agt<br>Glu Lys Ser His Pro Arg Ser Pro Asn Val Leu Ser Val Ala Leu Ser<br>685              690              695 | 2116 | |
| caa aga act aca gtt cct gag gaa gaa cta aat cca aag ata cta gct<br>Gln Arg Thr Thr Val Pro Glu Glu Glu Leu Asn Pro Lys Ile Leu Ala<br>700              705              710 | 2164 | |
| ttg cag aat gct cag aga aag cga aaa atg gaa cat gat ggt tca ctt<br>Leu Gln Asn Ala Gln Arg Lys Arg Lys Met Glu His Asp Gly Ser Leu<br>715              720              725 | 2212 | |
| ttt caa gca gta gga att gga aca tta tta cag cag cca gac gat cat<br>Phe Gln Ala Val Gly Ile Gly Thr Leu Leu Gln Gln Pro Asp Asp His<br>730              735              740 | 2260 | |
| gca gct act aca tca ctt tct tgg aaa cgt gta aaa gga tgc aaa tct<br>Ala Ala Thr Thr Ser Leu Ser Trp Lys Arg Val Lys Gly Cys Lys Ser<br>745              750              755              760 | 2308 | |

-continued

```
agt gaa cag aat gga atg gag caa aag aca att att tta ata ccc tct      2356
Ser Glu Gln Asn Gly Met Glu Gln Lys Thr Ile Ile Leu Ile Pro Ser
                765                 770                 775 gat tta gca tgt aga ctg ctg ggg caa tca atg gat gaa agt gga tta      2404
Asp Leu Ala Cys Arg Leu Leu Gly Gln Ser Met Asp Glu Ser Gly Leu
            780                 785                 790 cca cag ctg acc agt tat gat tgt gaa gtt aat gct cct ata caa ggc      2452
Pro Gln Leu Thr Ser Tyr Asp Cys Glu Val Asn Ala Pro Ile Gln Gly
        795                 800                 805 agc aga aac cta ctg cag ggt gaa gaa tta ctc aga gct ttg gat caa      2500
Ser Arg Asn Leu Leu Gln Gly Glu Glu Leu Leu Arg Ala Leu Asp Gln
    810                 815                 820 gtt aac tgagctttt cttaatttca ttcctttttt tggacactgg tggctcacta        2556
Val Asn
825 cctaaagcag tctatttata ttttctacat ctaattttag aagcctggct acaatactgc    2616 acaaacttgg ttagttcaat ttttgatccc ctttctactt aatttacatt aatgctcttt    2676 tttagtatgt tctttaatgc tggatcacag acagctcatt ttctcagttt tttggtattt    2736 aaaccattgc attgcagtag catcattaat taaaaaatgc acctttttat ttatttattt    2796 ttggctaggg agtttatccc ttttttcgaat tatttttaag aagatgccaa tataatttt    2856 gtaagaaggc agtaaccttt catcatgatc ataggcagtt gaaaaatttt tacacctttt    2916 ttttcacaaa ttttacataa ataataatgc tttgccagca gtacgtggta gccacaattg    2976 cacaatatat tttcttaaaa aataccagca gttactcatg aaatatattc tgcgtttata    3036 aaactagttt ttaagaagaa attttttttg cctatgaaaa ttgttaaaca actggaacat    3096 gacattgtta atcatataat aatgattctt aaatgctgta tggtttatta tttaaatggg    3156 taaagccatt tacataatat agaaagatat gcatatatct gaaggtatg tggcatttat     3216 ttggataaaa ttctcaattc agagaaatca aatctgatgt ttctatagtc actttgccag    3276 ctcaaaagaa aacaataccc tatgtagttg tggaagttta tgctaatatt gtgtaactga    3336 tattaaacct aaatgttctg cctaccctgt tggtataaag atattttgag cagactgtaa    3396 acaagaaaaa aaaaaaatca tgcattctta gcaaaattgc ctagtatgtt aatttgctca    3456 aaatacaatg tttgatttta tgcactttgt cgctattaac atccttttt tcatgtagat    3516 ttcaataatt gagtaatttt agaagcatta ttttaggaat atatagttgt caaaaacagt    3576 aaatatcttg ttttttctat gtacattgta caaattttc attccttttg ctctttgtgg     3636 ttggatctaa cactaactgt attgttttgt tacatcaaat aaacatcttc tgtggaaaaa    3696 aaaaaaaaa aaaaaaaaa aaaaaaaaa aaaaaaaa                                3736
```

<210> SEQ ID NO 2
<211> LENGTH: 826
<212> TYPE: PRT
<213> ORGANISM: Homo sapiens

<400> SEQUENCE: 2

```
Met Glu Gly Ala Gly Gly Ala Asn Asp Lys Lys Lys Ile Ser Ser Glu
  1               5                  10                  15

Arg Arg Lys Glu Lys Ser Arg Asp Ala Ala Arg Ser Arg Arg Ser Lys
             20                  25                  30

Glu Ser Glu Val Phe Tyr Glu Leu Ala His Gln Leu Pro Leu Pro His
         35                  40                  45

Asn Val Ser Ser His Leu Asp Lys Ala Ser Val Met Arg Leu Thr Ile
     50                  55                  60
```

-continued

```
Ser Tyr Leu Arg Val Arg Lys Leu Leu Asp Ala Gly Asp Leu Asp Ile
 65                  70                  75                  80

Glu Asp Asp Met Lys Ala Gln Met Asn Cys Phe Tyr Leu Lys Ala Leu
             85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480
```

-continued

```
Asn Pro Glu Ser Leu Glu Leu Ser Phe Thr Met Pro Gln Ile Gln Asp
            485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
        530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Thr Ala Thr Thr Asp Glu Leu
610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
        690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Glu Gln Asn Gly Met Glu Gln
        755                 760                 765

Lys Thr Ile Ile Leu Ile Pro Ser Asp Leu Ala Cys Arg Leu Leu Gly
        770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825
```

HYPOXIA-INDUCIBLE FACTOR 1ALPHA VARIANTS AND METHODS OF USE

CROSS REFERENCE TO RELATED APPLICATIONS

This application claims the benefit of U.S. Provisional Application No. 60/465,565, which was filed on Apr. 25, 2003.

FIELD OF INVENTION

The invention relates to the identification and use of agents which can effect oxygen homeostasis through modulation of Hypoxia-Inducible Factor 1α and its physiological functions.

BACKGROUND

Hypoxia-inducible factor 1 (HIF-1) is a heterodimeric transcription factor that plays a critical role in regulating mammalian oxygen homeostasis (Bunn, et al (1996) *Physiol Rev* 76(3), 839–85; Semenza, (1999) *Annu Rev Cell Dev Biol* 15, 551–78; Wenger, (2000) *J Exp Biol* 203 Pt 8, 1253–63). Adaptation to changes in oxygen tension involves a variety of developmental, physiological, and pathophysiological processes including embryonic development, angiogenesis, cerebral and myocardial ischemia, and tumorigenesis (Semenza, (2000) *Genes Dev* 14(16), 1983–91; Semenza, (2002) *Trends Mol Med* 8(4), S62–7) HIF-1 consists of HIF-1α and HIF-1β subunits, both of which belong to the basic helix-loop-helix Per-AhR-Sim family (Wang, et al (1995) *J Biol Chem* 270(3), 1230–7; Wang, et al (1995) *Proc Natl Acad Sci USA* 92(12), 5510–4). Under hypoxia, HIF-1 becomes activated and up-regulates target genes such as erythropoietin, vascular endothelial growth factor, glucose transporter, and glycolytic enzymes (Semenza, (1999) *Annu Rev Cell Dev Biol* 15, 551–78).

HIF-1 activation is regulated primarily by the accumulation of HIF-1 alpha protein (Huang, et al H. F. (1996) *J Biol Chem* 271(50), 32253–9). Both HIF-1 alpha and HIF-1 beta genes are constitutively expressed in many cell lines examined (Huang, et al (1996) *J Biol Chem* 271(50), 32253–9; Gradin, et al (1996) *Mol Cell Biol* 16(10), 5221–31; Wood, et al (1996) *J Biol Chem* 271(25), 15117–23; Kallio, et al (1997) *Proc Natl Acad Sci USA* 94(11), 5667–72), whereas HIF-1α protein is constantly degraded under normoxia by the ubiquitin-proteasome pathway (Huang, et al (1998) *Proc Natl Acad Sci USA* 95(14), 7987–92; Kallio, et al (1999) *J Biol Chem* 274(10), 6519–25). The degradation is controlled by a unique oxygen-dependent degradation domain (ODD) consisting of ~200 amino acids within HIF-1α (Huang, et al (1998) *Proc Natl Acad Sci USA* 95(14), 7987–92). Deletion of the entire ODD gave rise to a stable HIF-1α, capable of heterodimerization, DNA-binding, and transactivation in cell culture systems. Consistently, the ODD-deleted HIF-1α (but not the full-length), when transgenically expressed in the mouse epidermis, activated HIF-1 target genes, thereby resulting in epidermal hypervascularity (Elson, et al (2001) *Genes Dev* 15(19), 2520–32), providing compelling evidence that a stable HIF-1α, irrespective of hypoxic signal, is sufficient for transcriptional activation in animal models.

Studies on the mechanisms underlying HIF-1α degradation, Maxwell et al. first reported that the tumor suppressor protein, VHL, targets HIF-1α for oxygen-dependent proteolysis in an iron-dependent way (Maxwell, et al (1999) *Nature* 399(6733), 271–5). Inactivation of the VHL (von Hippel-Lindau) gene is linked to the development of the VHL disease, a hereditary human cancer syndrome characterized by the predisposition to develop highly angiogenic tumors (Kaelin, et al (1998) *Trends Genet* 14(10), 423–6). The VHL protein is in a multiprotein complex with elongin B, elongin C, and Cul2, which share sequence similarity with the Skp1 and Cdc53 components of the SCF ubiquitin ligase (Duan, et al (1995) *Science* 269(5229), 1402–6; Kibel, et al (1995) *Science* 269(5229), 1444–6; Pause, et al (1997) *Proc Natl Acad Sci USA* 94(6), 2156–61; Stebbins, et al (1999) *Science* 284(5413), 455–61). Furthermore, VHL is associated with Rbx1 or ROC1 (Kamura, et al (1999) *Science* 284(5414), 657–61), a potent SCF ubiquitin ligase activator that facilitates degradation of substrate proteins by recruiting a ubiquitin-conjugating enzyme to the complex (Ohta, et al (1999) *Mol Cell* 3(4), 535–41; Tan, et al (1999) *Mol Cell* 3(4), 527–33). All these observations have led to the hypothesis that the VHL complex functions as an E3 ubiquitin ligase for HIF-1α polyubiquitination (Kamura, et al (2000) *Proc Natl Acad Sci USA* 97(19), 10430–5) by specifically targeting the ODD of HIF-1α (Cockman, et al (2000) *J Biol Chem* 275(33), 25733–25741; Ohh, et al (2000) *Nat Cell Biol* 2(7), 423–427; Tanimoto, et al (2000) *Embo J* 19(16), 4298–4309).

VHL binding requires specific recognition of hydroxylated Pro-564 of HIF-1α (Ivan, et al (2001) *Science* 292(5516), 464–8.; JAAkkola, et al (2001) *Science* 292(5516), 468–72.; Yu, et al (2001) *Proc Natl Acad Sci USA* 98(17), 9630–5). Proline hydroxylation, catalyzed by a conserved family of prolyl-4-hydroxylases, relies on molecular oxygen and iron (Epstein, et al (2001) *Cell* 107(1), 43–54.; Bruick, R. K., and McKnight, S. L. (2001) *Science* 294(5545), 1337–40), indicating these enzymes act as oxygen sensors. Moreover, recent studies of HIF1α-VHL complexes provide a structural basis for VHL recognition of hydroxyproline in HIF-1α (Hon, et al (2002) *Nature* 417(6892), 975–8.; Min, et al (2002) *Science* 296(5574), 1886–9), suggesting a central role for proline hydroxylation in oxygen signaling. Interestingly, Pro-402 of HIF-1α is also subjected to hydroxylation and, in turn, targeted by the VHL E3 ubiquitin ligase for HIF-1α ubiquitination (Masson, et al (2001) *Embo J* 20(18), 5197–206).

SUMMARY OF THE INVENTION

Despite the identification of a crucial role for Pro-564 in controlling HIF-1α degradation, it has also been demonstrated that partial deletion of the ODD containing Pro-564 failed to completely stabilize HIF-1α (Huang, et al. (1998) *Proc Natl Acad Sci USA* 95(14), 7987–92), indicating functional redundancy within the ODD. Since we know that Pro-564 is necessary but not sufficient for VHL binding, it would be important to discover what additional structural requirements there are for VHL binding and VHL-mediated degradation. Identification of methods and/or agents capable of modulating VHL binding at these required binding sites and, consequently, VHL-mediated degradation of HIF-1α, would be beneficial in the treatment of medical conditions involving oxygen homeostasis.

The present invention relates to the finding that Leu-574 is indispensable to VHL binding in vitro and in vivo, and to VHL-mediated degradation. This finding is based on the evidence that i) unlike Gal4-HIF1α(498–603), Gal4-HIF1α(498–573) is unable to bind to VHL, and is therefore constitutively expressed; ii) the addition of Leu-574 to Gal4-HIF1α(498–573) results in a gain of VHL binding and a loss of protein stability; iii) the mutation of Leu-574 in Gal4-HIF1α(498–603) leads to a decrease in VHL binding, and an increase in protein stability; and iv) Leu-574 is highly conserved in HIF-1α, HIF-2α, and HIF-3α. Therefore, Leu-574 plays a specific and crucial role in the VHL-dependent degradation pathway.

We have now discovered unique variant forms of HIF-1 alpha. polypeptide that are stable under hypoxic and non-hypoxic conditions.

In one embodiment, the invention relates to an isolated polypeptide having an amino acid sequence as set forth in SEQ ID NO: 2 wherein amino acid 574 is changed from leucine to any other amino acid. Isolated polynucleotides encoding such a polypeptide as well as antibodies which preferentially bind this polypeptide are also provided in a particular embodiment.

In another embodiment, the invention provides an isolated polypeptide having an amino acid sequence as set forth in SEQ ID NO: 2 wherein amino acid 574 is changed from leucine to any other amino acid; and amino acid 402 is changed from proline to any other amino acid, amino acid 564 is changed from proline to any other amino acid or the prolines at both positions 402 and 564 are changed to any other amino acid. Isolated polynucleotides encoding such a polypeptide as well as antibodies which preferentially bind this polypeptide are also provided in a particular embodiment.

In a further embodiment, the invention provides an isolated polypeptide having an amino acid sequence as set forth in SEQ ID NO: 2 wherein amino acids 574 is deleted therefrom. Isolated polynucleotides encoding such a polypeptide as well as antibodies which preferentially bind this polypeptide are also provided in a particular embodiment.

In still another embodiment, the invention provides an isolated polypeptide having an amino acid sequence as set forth in SEQ ID NO: 2 wherein amino acid 574 is deleted therefrom; and amino acid 402 is changed from proline to any other amino acid; amino acid 564 is changed from proline to any other amino acid or the prolines at both positions 402 and 564 are changed to any other amino acid. Isolated polynucleotides encoding such a polypeptide as well as antibodies which preferentially bind this polypeptide are also provided in a particular embodiment.

In an additional embodiment, a method is provided for treating a hypoxia-related tissue damage in a subject, by administering to the subject a therapeutically effective amount of a nucleotide sequence comprising an expression control sequence operatively linked to a polynucleotide having a sequence as set forth in SEQ ID NO: 1 encoding a polypeptide, wherein amino acid 574 is deleted therefrom or changed from leucine to any other amino acid.

In another embodiment, the invention provides a method of treating a hypoxia-related tissue damage in a subject by administering to the subject a therapeutically effective amount of a polypeptide having a sequence as set forth in SEQ ID NO: 2, wherein amino acid 574 is deleted therefrom or changed from leucine to any other amino acid.

Specific indications which would benefit from modulating the stability of HIF-1 alpha include 1) those diseases or disorders which would benefit from a promotion of angiogenesis, as in myocardial infarction, cardiac arrythmias, stroke, autoimmune diseases, neurodegenerative disorders and, in general, conditions caused by excessive cell death (i.e., apoptosis and necrosis), as well as 2) those conditions which would benefit from inhibition of angiogenesis, as in many forms of cancer, arthritis, diabetic retinopathy and certain inflammatory disorders.

In a further embodiment, the invention provides a composition for administration of stable human hypoxia inducible factor-1 alpha (HIF-1 alpha) polypeptide to a patient having hypoxia related tissue damage. The composition includes an isolated polypeptide having a sequence as set forth in SEQ ID NO: 2, wherein amino acid 574 is deleted therefrom or changed from leucine to any other amino acid and a pharmaceutically acceptable carrier.

The invention also provides compositions for administering a polynucleotide encoding stable human hypoxia inducible factor-1 alpha to a patient having hypoxia-related tissue damage, including a therapeutically effective amount of a nucleic acid sequence comprising an expression control sequence operatively linked to a polynucleotide having a sequence as set forth in SEQ ID NO: 1 encoding a polypeptide, wherein amino acid 574 is deleted therefrom or changed from leucine to any other amino acid; and a pharmaceutically acceptable carrier.

The present invention relates to DNA vectors that contain nucleotide sequences encoding HIF-1α variants of the invention. The DNA vectors may encode HIF-1α variants of the invention under the control of regulatory elements.

The invention also relates to in vivo delivery applications for gene therapy, including methods of administering engineered viral vectors or liposomes which contain DNA sequences encoding HIF-1α variants of the invention. The invention relates to ex vivo gene therapy approaches to provide engineered cells derived from a patient, or a compatible host, to express HIF-1α variants of the invention.

The present invention further relates to genetically engineered host cells which express HIF-1α variants of the invention. The host cells may be genetically engineered in vitro or in vivo.

The invention also provides for a method for identifying patients at risk of having or developing a condition associated with impaired oxygen homeostasis comprising detecting a mutation in an HIF-1α polypeptide at amino acid residue 574, wherein the presence of an amino acid other than Leu at this position is associated with increased risk of having or developing the condition.

The invention also provides a method for screening and identifying modulators, e.g., candidate or test compounds or agents (e.g., peptides, peptidomimetics, small molecules, or other drugs) which have a increase or decrease in the stability of wild-type HIF-1 alpha.

Other aspects of the invention are discussed infra.

BRIEF DESCRIPTION OF THE FIGURES

FIG. 1 represents depictions of gels demonstrating that VHL binds to both N-terminal and C-terminal ODD, wherein FIG. 1a illustrates the binding of anti-VHL antibody to wild-type HIF-1α under hypoxic conditions; wherein FIG. 1b is a schematic representation of constructs expressing wild-type HIF-1α and deletion mutants 401Δ603, 497Δ601, Pro-402, Pro-564 and the ODD where denoted; and wherein

FIG. 2 represents illustrations and data characterizing the ODD, wherein FIG. 2a is schematic representation of Gal4-ODD fusions that are serially deleted from the N-terminal and the C-terminal, where both Pro-402 and Pro-564, the N-terminal ODD (N-ODD), the C-terminal ODD (C-ODD), and the N-terminal activation domain (NAD) are indicated; wherein FIG. 2b represents immunoprecipitation-Western blot analysis of the Gal4-ODD deletion mutants expressed in 293 cells under normoxic and hypoxic conditions; and wherein

FIG. 3 depicts gels demonstrating VHL binding in vivo requires amino acids 574–603 of HIF-1α, wherein

FIG. 7 illustrates that Leu-574 of HIF-1α is required for prolyl hydroxylation wherein A) HIF-1α and its proline mutants, as indicated, were transiently expressed in 293 cells; after 4-h Cbz-LLL treatment, their hydroxylation status was determined by Western blot with an antibody against Hyp-564 (α-Hyp-564, top), while their expression levels were analyzed by an antibody against HIF-1α (α-HIF-1 ca bottom); B) non-hydroxylated and hydroxylated HIF-1 a were in vitro translated, respectively, in the presence of DFO or FeCl$_2$; the translated products were loaded at increasing amounts (0.17, 0.33, and 0.5 μl), and subjected to Western blot with the anti-Hyp-564 (top two panels) and the anti-HIF-1α (bottom) antibodies; autoradiography with different exposure time (in seconds) was indicated; C,D) HIF-1α and L574S mutant were evaluated for prolyl hydroxylation under normoxic and DFO-treated conditions with indicated antibodies (B); ratio of HIF-1α containing Hyp-564 to the total amount of HIF-1α (Hyp-564/HIF-1α), as determined by densitometry, was presented in a bar graph as means plus standard errors from 3 independent experiments (C); the signal intensity is specified at the bottom of each lane.

DETAILED DESCRIPTION OF THE INVENTION

Figure 1A:
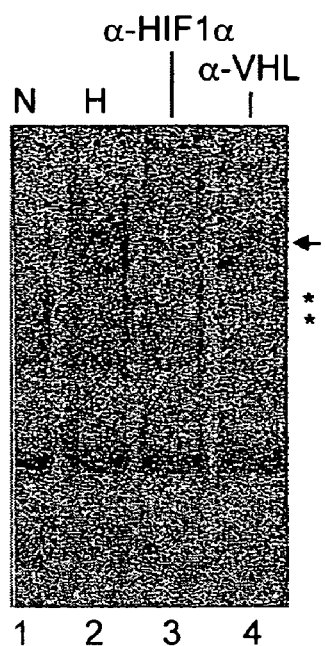

The invention provides an isolated stable hypoxia-inducible factor-1 alpha (V574HIF-1 alpha) variant. V574 HIF-1 alpha polypeptide has a sequence as set forth in SEQ ID NO: 2, wherein amino acid at position 574 is deleted therefrom or changed from a leucine to any other amino acid. In addition, the present invention also provides for other stable hypoxia-inducible factor-1 alpha variants which include amino acid substitutions at positions 402 and 564 in which the proline residues at these positions are substituted for any other amino acids. The term "V574HIF-1α variants" includes HIF-1α molecules with a deletion or substitution at amino acid position 574 and other variants which have additional amino acid substitutions at positions 402 and/or 564.

The invention provides methods for treatment of HIF-1-mediated disorders, including hypoxia-mediated tissue damage, which are improved or ameliorated by modulation of HIF-1 protein stability. The term "modulate" envisions decreasing the stability of HIF-1 when desirable, or increasing the stability of HIF-1 when appropriate.

Increasing the stability of HIF-1 would be desirable in conditions which would benefit from a promotion of angiogenesis, as in such diseases and disorders as myocardial infarction, cardiac arrythmias, stroke, autoimmune diseases, neurodegenerative disorders and, in general, conditions caused by excessive cell death (i.e., apoptosis and necrosis).

Decreasing the stability of HIF-1 would be an appropriate measure in treating which would benefit from inhibition of angiogenesis, as in such diseases and disorders as many forms of cancer, arthritis, diabetic retinopathy and certain inflammatory disorders.

I. Compositions of V574HIF-1α Variants

According to the methods of the invention, the isolated polypeptide V574HIF-1α or the nucleotide sequence encoding V574HIF-1α is introduced into a human patient for the treatment or prevention of HIF-1-mediated disorders. The appropriate human patient is a subject suffering from a HIF-1-mediated disorder or a hypoxia-related disorder, such as atherosclerotic coronary or cerebral artery disease. When a patient is treated with nucleotide, the nucleotide can be a sequence which encodes V574HIF-1 alpha or a nucleotide sequence which encodes V574HIF-1 alpha and a nucleotide sequence which encodes HIF-1 beta (see, for example, Rayes, et al., Science, 256:1193–1195, 1992; and Hoffman, et al., Science, 252:954–958, 1991).

A) Polypeptides and Nucleic Acids:

The invention provides an isolated V574HIF-1 alpha polypeptide characterized as having having essentially the amino acid sequence of SEQ ID NO: 2 with the exception of the leucine residue at position 574 being absent (deleted) or changed to any other amino acid; and capable of dimerizing to HIF-1 beta to form HIF-1. The term "isolated" as used herein refers to V574HIF-1 alpha which is substantially free of other proteins, lipids, carbohydrates or other materials with which it is naturally associated. One skilled in the art can purify V574HIF-1.alpha using standard techniques for protein purification. The isolated polypeptide will yield a single band on a non-reducing polyacrylamide gel. The purity of the V574HIF-1 alpha polypeptide can also be determined by amino-terminal amino acid sequence analysis. V574HIF-1 alpha protein includes functional fragments of the polypeptide, as long as the activity of HIF-1.alpha, such as the ability to bind with HIF-1 beta, remains. Fragments or smaller peptides containing the biological activity of V574HIF-1 alpha in terms of increased stability are included in the invention.

In one embodiment, the invention relates to an isolated polypeptide having an amino acid sequence as set forth in SEQ ID NO: 2 wherein amino acid 574 is changed from leucine to any other amino acid. In another embodiment, the invention provides an isolated polypeptide having an amino acid sequence as set forth in SEQ ID NO: 2 wherein amino acid 574 is changed from leucine to any other amino acid, and amino acid 402 is changed from proline to any other amino acid, amino acid 562 is changed from proline to any other amino acid or the prolines at both positions 402 and 564 are changed to any other amino acid.

The invention provides nucleotide sequences encoding the V574HIF-1 alpha polypeptide (SEQ ID NO: 1) wherein the codon at amino acid position 574 is deleted or substituted for another codon encoding any other amino acid. The invention also provides for nucleotide sequences encoding V574HIF-1α variants wherein there are additional codon substitutions at amino acid positions 402 and 564. These nucleotides include DNA, cDNA, and RNA sequences which encode V574HIF-1 alpha. It is also understood that all nucleotide sequences encoding all or a portion of V574HIF-1 alpha are also included herein, as long as they encode a polypeptide with HIF-1 alpha activity and the codon for amino acid position 574 is deleted or changed to a codon encoding any other amino acid. Such nucleotide sequences include synthetic, and intentionally manipulated nucleotide sequences. For example, HIF-1 alpha nucleotide sequences may be subjected to site-directed mutagenesis.

The nucleotide sequences of the invention include sequences that are degenerate as a result of the genetic code. All degenerate nucleotide sequences are included in the invention as long as the amino acid sequence of V574HIF-1 alpha polypeptide which is encoded by the nucleotide sequence is functionally unchanged in terms of increased stability.

Minor modifications of the V574HIF-1 alpha primary amino acid sequence may result in proteins which have substantially equivalent activity as compared to the V574HIF-1 alpha polypeptide described herein. Such proteins include those as defined by having essentially the amino acid sequence of SEQ ID NO: 2 with the deletion or substitution of the leucine at position 574 for any other amino acid. Such modifications may be deliberate, as by site-directed mutagenesis, or may be spontaneous. All of the polypeptides produced by these modifications are included herein as long as the biological activity of V574HIF-1.alpha. still exists. Further, deletions of one or more amino acids can also result in modification of the structure of the resultant molecule without significantly altering its biological activity. This can lead to the development of a smaller active molecule which would have broader utility. For example, one can remove amino or carboxy terminal amino acids which are not required for V574HIF-1 alpha biological activity with increased stability.

The V574HIF-1.alpha. polypeptide of the invention encoded by the nucleotide sequence of the invention includes the disclosed sequence (SEQ ID NO: 2) with the deletion or substitution of the leucine at position 574 for any other amino acid and conservative variations thereof. The term "conservative variation" as used herein denotes the replacement of an amino acid residue by another, biologically similar residue. Examples of conservative variations include the substitution of one hydrophobic residue such as isoleucine, valine, leucine, or methionine for another, or the substitution of one solar residue for another, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on cDNA using primers capable of annealing to the DNA sequence of interest, and 3) site-directed mutagenesis.

B) Recombinant Expression Vectors and Host Cells

Another aspect of the invention pertains to vectors, preferably expression vectors, containing an V574HIF-1 alpha nucleic acid or a portion thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule of the invention in a form suitable for expression of the nucleic acid molecule in a host cell. For example, the recombinant expression vectors can include one or more regulatory sequences, selected on the basis of the host cells to be used for expression, operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described in, for example, Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., V574HIF-1 alpha proteins, other variant forms of V574HIF-1 alpha proteins, fusion proteins, and the like).

The recombinant expression vectors of the invention can be designed for expression of V574HIF-1 alpha variants in prokaryotic or eukaryotic cells. For example, V574HIF-1 alpha variants can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

One strategy to maximize recombinant protein expression in E. coli is to express the variant in a bacterial host with an impaired capacity to proteolytically cleave the recombinant protein (Gottesman, S., Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111–2118). Such alteration of nucleic acid sequences of the invention can be carried out by standard DNA synthesis techniques.

In another embodiment, the V574HIF-1 alpha expression vector is a yeast expression vector. Examples of vectors for expression in yeast S. cerivisae include pYepSec1 (Baldari, et al., (1987) Embo J. 6:229–234), pMFa (Kurjan and Herskowitz, (1982) Cell 30:933–943), pJRY88 (Schultz et al., (1987) Gene 54:113–123), pYES2 (Invitrogen Corporation, San Diego, Calif.), and picZ (InVitrogen Corp, San Diego, Calif.

Alternatively, V574HIF-1 alpha variants can be expressed in insect cells using baculovirus expression vectors. Baculovirus vectors available for expression of proteins in cultured insect cells (e.g., Sf9 cells) include the pAc series (Smith et al. (1983) Mol. Cell Biol. 3:2156–2165) and the pVL series (Lucklow and Summers (1989) Virology 170: 31–39.

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid molecule preferentially in a particular cell type (e.g., tissue-specific regulatory elements are used to express the nucleic acid molecule). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374–379) and the alpha-fetoprotein promoter (Campes and Tilghman (1989) Genes Dev. 3:537–546.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to V574HIF-1 alpha mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an HIF-1 alpha variant can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an HIF-1 alpha protein or can be introduced on a separate vector. Cells stably transfected with the introduced nucleic acid can be identified by drug selection (e.g., cells that have incorporated the selectable marker gene will survive, while the other cells die.

A host cell of the invention, such as a prokaryotic or eukaryotic host cell in culture, can be used to produce (i.e., express) an V574HIF-1 alpha variant. Accordingly, the invention further provides methods for producing an V574HIF-1 alpha variant using the host cells of the invention. In one embodiment, the method comprises culturing the host cell of invention (into which a recombinant expression vector encoding an V574HIF-1 alpha variant has been introduced) in a suitable medium such that an V574HIF-1 alpha variant is produced. In another embodiment, the method further comprises isolating an V574HIF-1 alpha variant from the medium or the host cell.

II. Methods of Treatment

The present invention provides for both prophylactic and therapeutic methods of treating a subject at risk of (or susceptible to) or having a disorder associated with aberrant HIF-1 alpha expression, activity or stability. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the V574HIF-1 alpha protein and nucleotide variants of the present invention or HIF-1 alpha stability modulators according to that individual's drug response genotype. Pharmacogenomics allow a clinician or physician to target prophylactic or therapeutic treatments to patients who will most benefit from the treatment and to avoid treatment of patients who will experience toxic drug-related side effects.

A) Prophylactic Methods

In one aspect, the invention provides a method for preventing in a subject, a disease or condition associated with an aberrant HIF-1 alpha stability, by administering to the subject V574HIF-1 alpha protein or nucleotide variants or an agent which modulates HIF-1 alpha stability. Subjects at risk for a disease which is caused or contributed to by aberrant HIF-1 alpha stability can be identified by, for example, any or a combination of diagnostic or prognostic assays as described herein. Administration of a prophylactic agent can occur prior to the manifestation of symptoms characteristic of the HIF-1 alpha aberrancy, such that a disease or disorder is prevented or, alternatively, delayed in its progression. Depending on the type of HIF-1 alpha aberrancy, for example, a V574HIF-1 alpha variant or agent which modulates HIF-1 alpha stability can be used for treating the subject. The appropriate agent can be determined based on screening assays described herein.

B) Therapeutic Methods

Another aspect of the invention pertains to methods of modulating HIF-1 alpha stability for therapeutic purposes. Accordingly, in an exemplary embodiment, the modulatory method of the invention involves contacting a cell with an agent which modulates (e.g., increases or deceases) endogenous HIF-1 alpha stability. In another embodiment, the method involves administering a V574HIF-1 alpha protein variant or nucleic acid molecule as therapy to compensate for reduced or aberrant HIF-1 alpha stability.

An increase of HIF-1 alpha stability is desirable in situations in which HIF-1 alpha is abnormally low and/or in which increased HIF-1 alpha activity is likely to have a beneficial effect. For example, an increase of HIF-1 alpha stability is desirable in situations in which increased HIF-1 alpha activity is likely to have a beneficial effect, e.g., in cases for promoting angiogenesis. Likewise, decreasing HIF-1 alpha stability is desirable in situations in which HIF-1 alpha is abnormally high and/or in which decreased HIF-1 alpha activity is likely to have a beneficial effect, e.g., in the case of many forms of cancer.

Angiogenesis, defined as the growth of new capillaries from pre-existing vessels, is a pervasive biological phenomenon that is at the core of many physiologic and pathologic processes (U.S. Pat. No. 5,318,957, incorporated by reference herein in its entirety.). Examples of physiologic processes which depend upon angiogenesis include embryogenesis, wound repair, repair of ischemic tissue damage and the ovarian/menstrual cycle. (Folkman et al., Science 235: 442–447 (1987)). In contrast, chronic inflammation associated with chronic fibroproliferative disorders as well as growth and metastasis of solid tumors are associated with aberrant angiogenesis, or an imbalance in the local microenvironmental ratio of the expression of angiogenic:angiostatic factors.

Increasing the stability of HIF-1 would be desirable in conditions which would benefit from a promotion of angiogenesis, as in such diseases and disorders as myocardial infarction, cardiac arrythmias, stroke, autoimmune diseases, neurodegenerative disorders and, in general, conditions caused by excessive cell death (i.e., apoptosis and necrosis).

Decreasing the stability of HIF-1 would be an appropriate measure in treating which would benefit from inhibition of angiogenesis, as in such diseases and disorders as many forms of cancer, arthritis, diabetic retinopathy and certain inflammatory disorders.

The invention includes methods for treating or preventing certain neurological disorders, including the consequences of stroke, heart attack and traumatic head or brain injury, epilepsy or neurodegenerative diseases comprising the administration of an effective amount of one or more compounds of the invention to a subject including a mammal, such as a primate, especially a human, in need of such treatment. In particular, the invention provides methods for treatment and/or prophylaxis of nerve cell death (degeneration) resulting e.g. from hypoxia, hypoglycemia, brain or spinal cord ischemia, brain or spinal cord trauma, stroke, heart attack or drowning. Typical candidates for treatment include, e.g., patients who have experienced or at risk for heart attack and/or stroke and/or persons suffering from cardiac arrest neurological deficits, brain or spinal cord injury patients, patients undergoing major surgery such as heart surgery where brain ischemia is a potential complication and patients such as divers suffering from decompression sickness due to gas emboli in the blood stream. Candidates for treatment also will include those patients undergoing a surgical procedure requiring extra-corporeal circulation such as, e.g., a bypass procedure. Subjects suffering from or susceptible to peripheral neuropathy can be treated in accordance with the invention by administration of an effective amount of one or more compounds as disclosed herein.

The invention in particular provides methods for treatment which comprise administration of one or more compounds of the invention to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurysm or hemorrhage. Thus, an effective amount of one or more compounds of the present invention could be administered pre-operatively or peri-operatively to reduce such risks associated with carotid endarterectomy, or other post-surgical neurological deficits.

The invention further includes methods for prophylaxis against neurological deficits resulting from, e.g., coronary artery bypass graft surgery and aortic valve replacement surgery, or other procedures requiring extra-corporeal circulation. Those methods will comprise administering to a patient undergoing such surgical procedures an effective amount of one or more compounds of the invention, typically either pre-operatively or peri-operatively.

Methods of the invention can be particularly useful in the treatment of mammalian subjects, e.g., humans, to provide neuroprotective therapy and/or prophylaxis. Typically, such subjects include those afflicted with neurodegenerative diseases such as Parkinson's disease, Huntington's disease, Amyotrophic Lateral Sclerosis, Alzheimer's disease, Down's Syndrome and Korsakoff's disease.

An agent that modulates HIF-1 alpha protein stability can be any agent which interacts with the Leu574 residue of HIF-1 alpha or interacts with the codon for amino acid position 547 of a nucleic acid encoding HIF-1 alpha, Agents can include nucleic acids or proteins, a modified naturally-occurring target molecule of an HIF-1 alpha protein (e.g., modified VHL), an HIF-1 alpha antibody targeted to the Leu574 residue or other small molecules which interact with the Leu574 residue to cause an increase or decrease in the binding of VHL and, consequently, increase or decrease the degradation of HIF-1 alpha.

These agents can be identified based on screening assays described herein. Alternatively, agents can be targeted to the Leu574 residue by in silico modeling, through the generation of peptide-specific binding reagents (e.g., antibodies and aptamers), by screening for agents that modulate the binding of VHL protein to a peptide comprising Leu574. In silico modeling of protein-ligand interactions are known in the art and are described in, for example, Lengauer et al., 1996, Curr. Opin. Struct. Biol. 5: 402–406; Strynadka et al., 1996, Nature Struct. Bio. 3: 233–239; Chen et al., 1997, Biochemistry 36: 11402–11407 (1997); and Kuntz et al., J. Mol. Biol. 161: 269–288 (1982); the entireties of which are incorporated by reference herein.

In addition, the above therapeutic agents of the present invention which modulate the stability of HIF-1 alpha can be co-administered with others agents which affect the stability of HIF-1 alpha by different mechanisms. For example, it is known that VHL-mediated degradation of HIF-1 alpha requires the hydroxylation of prolines in amino acid positions 402 and 564. Agents which interfere with the binding of VHL to the Leu574 site of HIF-1 alpha and thereby decrease its degradation can be co-administered with agents that act as proline hydroxylase inhibitors, such as, ferrous ion chelators, cobalt chloride and 2-oxy-glutarate.

The proline hydroxylase inhibitors will act to augment the decrease in degradation of HIF-1 alpha.

III. Gene Therapy and Other Approaches for Delivering V574HIF-1α Variant Nucleotides The present invention also provides gene therapy for the treatment of hypoxia-related disorders, which are improved or ameliorated by the V574HIF-1 polypeptide. Such therapy would achieve its therapeutic effect by introduction of the V574HIF-1 alpha nucleotide, alone or in combination with HIF-1 beta nucleotide, into cells exposed to hypoxic conditions. Delivery of V574HIF-1 alpha nucleotide, alone or in combination with HIF-beta nucleotide, can be achieved using a recombinant expression vector such as a chimeric virus or a colloidal dispersion system. Especially preferred for therapeutic delivery of sequences is the use of targeted liposomes.

Various viral vectors which can be utilized for gene therapy as taught herein include adenovirus, adeno-associated virus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a V574HIF-1 alpha variant sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the V574HIF-1 alpha variant nucleotide sequence.

Another targeted delivery system for V574HIF-1 alpha variant nucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LW), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al. (1981) Trends Biochem. Sci. 6:77). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al. (1988) Biotechniques 6:682).

The composition of the liposome is usually a combination of phospholipids, particularly high-phase-transition-temperature phospholipids, usually in combination with sterols, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidyl-glycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and. distearoylphosphatidylcholine.

IV. Predictive Medicine

The present invention pertains to the field of predictive medicine in which diagnostic assays and prognostic assays are used for prognostic (predictive) purposes to thereby treat an individual prophylactically. Accordingly, one aspect of the present invention relates to diagnostic assays for determining a mutation in the nucleic acid of HIF-1 alpha at amino acid position 574, in the context of a biological sample (e.g., blood, serum, cells, or tissue) to thereby determine whether a subject is afflicted with a disease or disorder, or is at risk of developing a disorder, associated with aberrant HIF-1 alpha stability. The invention also provides for prognostic (or predictive) assays for determining whether an individual is at risk of developing a disorder associated with HIF-1 alpha protein, nucleic acid activity or stability due to a mutation at amino acid position 574 of HIF-1 alpha (AA574 mutant HIF-1 alpha). For example, mutations in an HIF-1 alpha gene can be assayed in a biological sample. Such assays can be used for prognostic or predictive purposes to, thereby, phophylactically treat a subject prior to the onset of a disorder characterized by or associated with an HIF-1 alpha protein, nucleic acid activity or stability.

These and other agents are described in further detail in the following sections.

A) Diagnostic Assays

An exemplary method for detecting the presence or absence of HIF-1 alpha nucleic acid or protein with a mutation at amino acid position 574 in a biological sample involves obtaining a biological sample from a test subject and contacting the biological sample with a compound or an agent capable of detecting the mutation at amino acid position 574 of HIF-1 alpha nucleic acid or protein (e.g., mRNA, genomic DNA, or antibody) such that the presence of HIF-1 alpha nucleic acid or protein is detected in the biological sample. A preferred agent for detecting HIF-1 alpha mRNA or genomic DNA is a labeled nucleic acid probe capable of hybridizing to HIF-1 alpha mRNA or genomic DNA. Other suitable probes for use in the diagnostic assays of the invention are described herein.

A preferred agent for detecting HIF-1 alpha protein with a mutation at amino acid position 574 is an antibody capable of binding to HIF-1 alpha protein with that mutation, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect HIF-1 alpha mRNA, genomic DNA, or protein in a biological sample in vitro as well as in vivo. For example, in vitro techniques for detection of AA574 mutant HIF-1 alpha mRNA include Northern hybridizations and in situ hybridizations. In vitro techniques for detection of AA574 mutant HIF-1 alpha protein include enzyme linked immunosorbent assays (ELISAs), Western blots, immunoprecipitations and immunofluorescence. In vitro techniques for detection of HIF-1 alpha genomic DNA include Southern hybridizations. Furthermore, in vivo techniques for detection of AA574 mutant HIF-1 alpha protein include introducing into a subject a labeled anti-HIF-1 alpha antibody. For example, the antibody can be labeled with a radioactive marker whose presence and location in a subject can be detected by standard imaging techniques.

In one preferred embodiment, allele specific oligonucleotide probes are provided which are capable of distinguishing AA574 mutant HIF-1 alpha mRNA's from wild type HIF-1 alpha mRNA's. In another embodiment, allele specific antibodies are provided which are capable of binding to AA574 mutant HIF-1 alpha polypeptides but not wild type HIF-1 alpha polypeptides.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting HIF-1 alpha mRNA, genomic DNA, or protein with a mutation at amino acid position 574, such that the presence of HIF-1 alpha mRNA genomic DNA or protein is detected in the biological sample, and comparing the presence of HIF-1 alpha mRNA, genomic DNA, or protein in the control sample with the presence of HIF-1 alpha mRNA, genomic DNA, or protein in the test sample.

The invention also encompasses kits for detecting the presence of AA574 mutant HIF-1 alpha in a biological sample. For example, the kit can comprise a labeled compound or agent capable of detecting AA574 mutant HIF-1 alpha DNA, mRNA, or protein in a biological sample; means for determining the amount of AA574 mutant HIF-1 alpha in the sample; and means for comparing the amount of AA574 mutant HIF-1 alpha in the sample with a standard. The compound or agent can be packaged in a suitable container. The kit can further comprise instructions for using the kit to detect AA574 mutant HIF-1 alpha nucleic acid or protein.

B) Prognostic Assays

The diagnostic methods described herein can furthermore be utilized to identify subjects having or at risk of developing a disease or disorder associated with aberrant HIF-1 alpha stability. For example, the assays described herein, such as the preceding diagnostic assays or the following assays, can be utilized to identify a subject having or at risk of developing a disorder associated with HIF-1 alpha protein stability, as such may occur in many forms of cancer. Thus, the present invention provides a method for identifying a disease or disorder associated with aberrant HIF-1 alpha stability, in which a test sample is obtained from a subject and AA574 mutant HIF-1 alpha nucleic acid (e.g., mRNA or genomic DNA) or protein is detected, wherein the presence of AA574 mutant HIF-1 alpha protein or nucleic acid is prognostic for a subject having or at risk of developing a disease or disorder associated with aberrant HIF-1 alpha stability. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., protein, nucleic acid, small molecule, or other drug candidate) to treat a disease or disorder associated with aberrant HIF-1 alpha stability. For example, such methods can be used to determine whether a subject can be effectively treated with an agent for a disorder involving increased angiogenesis, e.g., cancer. Thus, the present invention provides methods for determining whether a subject can be effectively treated with an agent for a disorder associated with aberrant HIF-1 alpha stability in which a test sample is obtained and AA574 mutant HIF-1 alpha protein or nucleic acid is detected (e.g., wherein the presence of AA574 mutant HIF-1 alpha nucleic acid or protein is diagnostic for a subject that can be administered the agent to treat a disorder associated with aberrant HIF-1 alpha stability).

The methods of the invention can also be used to detect genetic alterations in an HIF-1 alpha gene at the codon encoding leucine at amino acid position 574, thereby determining if a subject with the altered gene is at risk for a disorder characterized by misregulation in HIF-1 alpha protein activity or nucleic acid expression, such as in some forms of cancer. In preferred embodiments, the methods include detecting, in a sample of cells from the subject, the presence or absence of a genetic alteration characterized by at least one of an alteration affecting the integrity of a gene encoding an HIF-1 alpha-protein. For example, such genetic alterations can be detected by ascertaining the existence of at least one of 1) a deletion of one or more nucleotides from an HIF-1 alpha gene; 2) an addition of one or more nucleotides to an HIF-1 alpha gene; 3) a substitution of one or more nucleotides of an HIF-1 alpha gene, 4) a chromosomal rearrangement of an HIF-1 alpha gene; 5) an alteration in the level of a messenger RNA transcript of an HIF-1 alpha gene, 6) aberrant modification of an HIF-1 alpha gene, such as of the methylation pattern of the genomic DNA, 7) the presence of a non-wild type splicing pattern of a messenger RNA transcript of an HIF-1 alpha gene, 8) a non-wild type level of an HIF-1 alpha-protein, 9) allelic loss of an HIF-1 alpha gene, and 10) inappropriate post-translational modification of an HIF-1 alpha-protein that may affect the amino acid at position 574 of HIF-1 alpha. As described herein, there are a large number of assays known in the art which can be used for detecting alterations in an HIF-1 alpha gene, including those as described in U.S. Pat. Nos. 6,506,568; 6,340,566; and 6,287,766. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the HIF-1 alpha-gene (see Abravaya et al. (1995) Nucleic Acids Res. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an AA574 mutant HIF-1 alpha gene under conditions such that hybridization and amplification of the HIF-1 alpha-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874–1878), transcriptional amplification system (Kwoh, D. Y. et al., (1989) Proc. Natl. Acad. Sci. USA 86:1173–1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In other embodiments, genetic mutations in HIF-1 alpha at amino acid position 574 can be identified by hybridizing a sample and control nucleic acids, e.g., DNA or RNA, to high density arrays containing hundreds or thousands of oligonucleotides probes (Cronin, M. T. et al. (1996) Human Mutation 7: 244–255; Kozal, M. J. et al. (1996) Nature Medicine 2: 753–759). For example, genetic mutations in HIF-1 alpha can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the HIF-1 alpha gene and detect mutations by comparing the sequence of the sample HIF-1 alpha with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO94/16101; Cohen et al. (1996) Adv. Chromatogr. 36:127–162; and Griffin et al. (1993) Appl. Biochem. Biotechnol. 38:147–159.

Other methods for detecting mutations in the HIF-1 alpha geneat the amino acid position 574 include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type HIF-1 alpha sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad Sci USA 85:4397; Saleeba et al. (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in HIF-1 alpha cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on an HIF-1 alpha sequence, e.g., a wild-type HIF-1 alpha sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in HIF-1 alpha genes at the amino acid position 574. For example, single strand conformation polymorphism (SSCP) may be used to detect differences in electrophoretic mobility between mutant and wild type nucleic acids (orita et al. (1989) Proc Natl. Acad Sci USA: 86:2766, see also Cotton (1993) Mutat. Res. 285:125–144; and Hayashi (1992) Genet. Anal. Tech. Appl. 9:73–79). Single-stranded DNA fragments of sample and control HIF-1 alpha nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an HIF-1 alpha gene with a mutation in the codon for the leucine amino acid at position 574.

Furthermore, any cell type or tissue in which HIF-1 alpha is expressed may be utilized in the prognostic assays described herein.

V. Screening Methods for Identifying Agents that Modulate the Stability of HIF-1α

The invention provides a method (also referred to herein as a "screening assay") for identifying modulators, e.g., candidate or test compounds or agents (e.g., peptides, peptidomimetics, small molecules, or other drugs) which have a stimulatory (increase) or inhibitory (decease) effect on VHL binding at the Leu-574 position of HIF-1 alpha and VHL-mediated degradation of HIF-1 alpha.

In one embodiment the invention provides a screening method method for identifying a modulator of an HIF-1 alpha polypeptide which alters its stability, comprising: 1) providing a polypeptide comprising an oxygen dependent degradation (ODD) domain, wherein the polypeptide consists of amino acid residues 1–574 of an HIF-1α polypeptide, or a biologically active portion thereof comprising Leu574, and optionally includes non-HIF-1α amino acids fused in frame to HIF-1α polypeptide sequences; 2) contacting the polypeptide with a compound; and 3) measuring an activity associated with oxygen dependent degradation of the polypeptide or the biologically active fragment thereof; and identifying as a modulator a compound that changes the activity.

In another embodiment, the invention provides a screening method for identifying agents that affect the degradation of HIF-1 alpha. The screening method comprises preparing and admixing an isolated preparation of a polypeptide having the amino acid sequence representing amino acids 1 through 574 of HIF-1 alpha with a test agent; and monitoring, by any suitable means, an inhibition of transcriptional activation of HIF-1 alpha, whereby a decrease of the transcriptional activation of HIF-1 alpha identifies an HIF-1 alpha inhibitor. This screening system can also be used to identify agents which increase the transcriptional activation of HIF-1 alpha. The screening method can be performed under normoxic and/or hypoxic conditions.

Use of these screening methods provides a means to determine agents/compounds that may alter the degradation of HIF-1 alpha. These screening method may be adapted to large-scale, automated procedures allowing for efficient high-volume screening of potential therapeutic agents.

In another embodiment, an assay is a cell-based assay in which a cell which expresses an HIF-1 alpha protein (with amino acids 1 through 574) is contacted with a test compound and the ability of the test compound to modulate HIF-1 alpha stability is determined. Determining the ability of the test compound to modulate HIF-1 alpha stability can be accomplished by monitoring, for example, the level of expression of up-regulated target genes such as erythropoeitin, vascular endothelial growth factor, glucose transporter and glycolytic enzymes. The cell, for example, can be of mammalian origin. The ability of the test compound to modulate the ability of HIF-1 alpha to bind to VHL can also be determined by, for example, coupling VHL with a radioisotope or enzymatic label such that binding of VHL to HIF-1 alpha can be determined by detecting the labeled VHL in a complex. For example, VHL can be labeled with $I^{125}$, $S^{35}$, $C^{14}$, or $H^3$, either directly or indirectly, and the radioisotope detected by direct counting of radioemmission or by scintillation counting. Alternatively, VHL can be enzymatically labeled with, for example, horseradish peroxidase, alkaline phosphatase, or luciferase, and the enzymatic label detected by determination of conversion of an appropriate substrate to product.

It is also within the scope of this invention to determine the ability of VHL to interact with HIF-1 alpha without the labeling of any of the interactants. For example, a microphysiometer can be used to detect the interaction of VHL without the labeling of either the VHL or the HIF-1 alpha. McConnell, H. M. et al. (1992) Science 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between VHL and HIF-1 alpha.

In another embodiment, the assay is a cell-free assay in which an HIF-1 alpha protein with amino acids 1 through 574 is contacted with a test compound and the ability of the test compound to modulate (e.g., increase or decrease) the stability of the HIF-1 alpha protein is determined. Determining the ability of the test compound to modulate the stability of an HIF-1 alpha protein can be accomplished, for example, by determining the ability of the HIF-1 alpha protein to bind to VHL by one of the methods described above for determining direct binding. Determining the ability of the HIF-1 alpha protein to bind to an HIF-1 alpha target molecule can also be accomplished using a technology such as real-time Biomolecular Interaction Analysis (BIA). Sjolander, S. and Urbaniczky, C. (1991) Anal. Chem. 63:2338–2345 and Szabo et al. (1995) Curr. Opin. Struct. Biol. 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting an HIF-1 alpha protein with amino acids 1 through 574 with VHL which binds the HIF-1 alpha protein to form an assay mixture, contacting the assay mixture with a test compound, and determining the ability of the test compound to interact with the leucine at amino acid position 574 of the HIF-1 alpha protein, wherein determining the ability of the test compound to interact with the HIF-1 alpha protein comprises determining the ability of the HIF-1 alpha protein to preferentially bind to or modulate the stability of an HIF-1 alpha target molecule.

In more than one embodiment of the above assay methods, it may be desirable to immobilize either HIF-1 alpha with amino acids 1 through 574 or VHL to facilitate separation of complexed from uncomplexed forms of one or both of the proteins, as well as to accommodate automation of the assay. Binding of a test compound to an HIF-1 alpha protein, or interaction of an HIF-1 alpha protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/HIF-1 alpha fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or HIF-1 alpha protein, and the mixture incubated under conditions conducive to complex formation (e.g., at physiological conditions for salt and pH). Following incubation, the beads or microtitre plate wells are washed to remove any unbound components, the matrix immobilized in the case of beads, and the presence and/or quantity of complex determined either directly or indirectly, for example, as described above. Alternatively, the complexes can be dissociated from the matrix, and the level of HIF-1 alpha binding or activity determined using standard techniques.

Other techniques for immobilizing proteins on matrices can also be used in the screening assays of the invention. For example, either an HIF-1 alpha protein or an HIF-1 alpha target molecule can be immobilized utilizing conjugation of biotin and streptavidin. Biotinylated HIF-1 alpha protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with HIF-1 alpha protein or target molecules but which do not interfere with binding of the HIF-1 alpha protein to its target molecule can be derivatized to the wells of the plate, and unbound target or HIF-1 alpha protein trapped in the wells by antibody conjugation. Methods for detecting such complexes, in addition to those described above for the GST-immobilized complexes, include immunodetection of complexes using antibodies reactive with the HIF-1 alpha protein or target molecule, as well as enzyme-linked assays which rely on detecting an enzymatic activity associated with the HIF-1 alpha protein or target molecule.

The test compounds of the present invention can be obtained using any of the numerous approaches in combinatorial library methods known in the art, including: biological libraries; spatially addressable parallel solid phase or solution phase libraries; synthetic library methods requiring deconvolution; the one-bead one-compound library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 35 12:145). Aptamer libraries may be generated as described in U.S. Pat. No. 6,423,493, U.S. Pat. No. 5,840, 867, Green and Janjic, *Biotechniques* (2000) 39(5): 1094–6 and Geyer and Brent, *Methods Enzymol* (2000) 328: 171–208.

Examples of methods for the synthesis of molecular libraries can be found in, for example, DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223, 409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.).

This invention further pertains to novel agents identified by the above-described screening assays. Accordingly, it is within the scope of this invention to further use an agent identified as described herein in an appropriate animal model. For example, an agent identified as described herein (e.g., an HIF-1 alpha modulating agent, an antisense HIF-1 alpha nucleic acid molecule, an HIF-1 alpha-specific antibody, or an HIF-1 alpha-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

VI. Pharmaceutical Compositions

The HIF-1 alpha nucleic acid molecules and HIF-1 alpha protein modulators (also referred to herein as "active compounds") of the invention can be incorporated into pharmaceutical compositions suitable for administration. Such compositions typically comprise the nucleic acid molecule or the protein modulator and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetrAAcetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an HIF-1 alpha nucleic acid molecule an HIF-1 alpha protein, or anti-HIF-1 alpha antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within-this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with written instructions for administration for the particular indication.

All documents mentioned herein are incorporated by reference in their entirety. The following examples are illustrative of the invention.

EXAMPLES

The following materials and methods were used in the Examples:

Cell Culture—293 and Hep3B cells were cultured in DMEM and MEM medium (Invitrogen), respectively, with 10% fetal bovine serum (Hyclone). For hypoxic treatment, cells were either incubated with 100 μM DFO (Sigma) or in a hypoxic chamber (NAPCO) maintaining 1% $O_2$ and 5% $CO_2$, balanced with $N_2$.

Plasmids. HIF-1α expression plasmids p(HA)HIF1α, p(HA)HIF1α(401Δ603), and p(HA)HIF1α(497Δ601) were described previously (Huang, et al (1998) Proc Natl Acad Sci USA 95(14), 7987–92). Gal4-HIF1α fusions were constructed by the standard PCR cloning method using specifically designed PCR primers that contain appropriate codons. All site-directed mutagenesis (and insertion and deletion mutations) was done using the QuikChange Site-Directed Mutagenesis kit (Stratagene) according to manufacturer's instructions, and were confirmed by DNA sequencing. pEpoE-Luc and pGal4-luc were described previously (Huang, L. E., Arany, Z., Livingston, D. M., and Bunn, H. F. (1996) Activation of hypoxia-inducible transcription factor depends primarily upon redox-sensitive stabilization of its alpha subunit. J Biol Chem 271, 32253–322596, 34; Hewitson, K. S., McNeill, L. A., Riordan, M. V., Tian, Y. M., Bullock, A. N., Welford, R. W., Elkins, J. M., Oldham, N.J., Bhattacharya, S., Gleadle, J. M., Ratcliffe, P. J., Pugh, C. W., and Schofield, C. J. (2002) Hypoxia inducible factor (HIF) asparagine hydroxylase is identical to factor inhibiting HIF (FIH) and is related to the cupin structural family. J Biol Chem 277, 26351–26355). pEYFP-Nuc was purchased from Clontech. V5/His-tagged expression plasmids encoding human prolyl hydroxylase HPH1, HPH2, and pHPH3, respectively, were kindly provided by Richard K. Bruick (University of Texas Southwestern Medical Center). p(HA)VHL was a gift of William G. Kaelin, Jr. (Dana-Farber Cancer Institute).

Transfection, Luciferase Assay, and Immunoprecipitation-Western blot analysis. Hep3B and 293 cells were cultured in 12-well and 6-well plates respectively, and transfected with Fugene 6 (Roche) as described previously (Gu, et al (2001) J Biol Chem 276(5), 3550–4). A typical transfection for luciferase assays contains 0.25 μg pGal4-luc, 0.1 μg effector plasmid, and 0.1 μg pEYFP-Nuc for normalizing transfection efficiency. Fluorescence and luciferase activities were sequentially scanned through a microplate fluorescence reader (FLx800, Bio-Tek), in which the Bright-Glo luciferase substrate (Promega) was used for luciferase reaction. For the determination of protein levels, 1 μg of Gal4-HIF-1α fusions were transfected into 293 cells. Twenty-four to forty hours after transfection, cells were lyzed in RIPA buffer [50 mM Tris (pH 7.5), 150 mM NaCl, 1 mM EDTA, 1% Nonidet P-40, 0.5% sodium deoxycholine, and 0.1% SDS]. Gal4 fusions were precipitated with polyclonal anti-Gal4 antibody (Santa Cruz) and were further probed with monoclonal anti-Gal4 antibody (Santa Cruz) in Western blot. All of the experiments were repeated 3–4 times.

In vitro translation and co-immunoprecipitations were performed as described previously (32). Briefly, the VHL protein, Gal4-C-ODD, and its variants were in vitro translated, respectively, according to the manufacturer's instructions (Promega). Five microliters of unlabeled VHL protein was mixed with 5 μl [$^{35}$S]methionine-labeled Gal4 fusions in NETN buffer containing 100 mM NaCl, 1 mM EDTA, 20 mM Tris (pH 8.0), and 0.5% Nonidet P-40. Two microliters of monoclonal anti-VHL antibody (BD Biosciences), together with Immobilized Recombinant Protein A agarose beads (Pierce), were added to the mix to a final volume of 250 μl. The reaction was incubated at 4° C. overnight, and the agarose beads were washed five times with the NETN buffer prior to SDS-polyacrylamide gel electrophoresis. The gel was subjected to Amplify fluorographic reagent (Amersham) before autoradiography.

To determine protein stability and hydroxylation status, 1 μg of various HIF-1α variants or Gal4-HIF-1α fusions were expressed in 293 cells grown in 6-well plates. pEYFP-Nuc (0.05 μg) was also included in some experiments for normalization of transfection efficiency. Cells were treated for 4 h with 100 μM DFO for hypoxic induction, or with 12.5 μM Cbz-LLL (Sigma) for protein stabilization. Whole cell extracts were prepared essentially as described previously (6). Anti-HIF-1α monoclonal antibody was purchased from BD Biosciences, anti-Gal4 monoclonal antibody from type protein expressed in normoxia was set arbitrarily to 1.

The hydroxylation status of Pro-564 was presented in a ratio of the hydroxylated form (Hyp-564) to the total amount of HIF-1α or Gal4 fusions. Densitometry was used to measure the intensity of the band with the LabWorks software (UVP). The plotted graph represents the results from three independent experiments. The ratio of the wild-type protein expressed in normoxia was set arbitrarily to 1.

Super-shift assay. Electrophoretic mobility shift assays were performed essentially as described previously (Huang, et al (1998) *Proc Natl Acad Sci USA* 95(14), 7987–92). A specific antibody (0.5–1 μl) was added to the DNA-binding reaction. Anti-VHL antibody was a gift of William G. Kaelin, Jr., and anti-Gal4 and anti-hemagglutinin antibodies were acquired as described previously (Huang, et al (1998) *Proc Natl Acad Sci USA* 95(14), 7987–92).

In vitro co-immunoprecipitation. Both VHL and Gal4 fusions were in vitro translated as described previously (Gu, et al (2001) *J Biol Chem* 276(5), 3550–4). [$^{35}$S]methionine-labeled Gal4 fusions were mixed with unlabeled VHL in NETN buffer (Gu, et al (2001) *J Biol Chem* 276(5), 3550–4) containing anti-VHL antibody. The reaction mixture was washed five times with NETN buffer before SDS-PAGE.

Generation of anti-Hyp-564 antibodies—For generation of antibodies that specifically recognize hydroxylated HIF-1α C-ODD, a peptide consisting amino acids 558–569 of human HIF-1α with a trans-4-hydroxy-S-proline residue at position 564 was synthesized. The peptide was conjugated to keyhole limpet hemocyanin and injected into rabbits. Specificity for hydroxylated HIF was tested by screening antisera against recombinant HIF-1α produced by in vitro translation in reticulocyte lysate (Promega) under conditions that support (100 μM FeCl$_2$) or inhibit (100 μM DFO) HIF-1α hydroxylation. An antiserum showing appropriate selectivity was obtained and is referred to here as anti-Hyp-564.

Prolyl hydroxylase binding assay—Gal4-C-ODD or the corresponding L574S mutant was transfected with or without V5-tagged HPH1, HPH2, or HPH3 expression plasmid. One microgram of each plasmid was used. After treatment with Cbz-LLL for 4 h, cells were lyzed in a buffer (35) containing 25 mM Tris (pH 7.5), 300 mM NaCl, and 1% Triton-X. The lysate was immunoprecipitated with anti-Gal4 polyclonal antibody (Santa Cruz), followed by immunoblotting with anti-V5 antibody (Invitrogen) and monoclonal anti-Gal4 antibody (Santa Cruz).

Example 1

VHL Binds to Both N-terminal and C-terminal ODD Independently

Hep3B cell extracts prepared from normoxic (N) or hypoxic (H) treatment were subjected to an electrophoretic mobility shift assay. Hypoxic cell extracts were also incubated with anti-HIF-1α (α-HIF1α) or anti-VHL (α-VHL) antibodies. The super-shifted complexes were indicated with an arrowhead, and HIF-1 DNA-binding activity marked with asterisks. Direct involvement of the VHL protein in HIF-1α degradation was first demonstrated by the addition of anti-VHL antibody (Maxwell, et al (1999) *Nature* 399 (6733), 271–5), which caused a super-shift of the slower (but not the faster) migrating HIF-1 DNA-binding activity (please see FIG. 1 where asterisks are marked in FIG. 1a, lane 4), while addition of anti-HIF1α antibody resulted in a complete shift of both HIF-1 binding activities (lane 3).

Figure 1B:
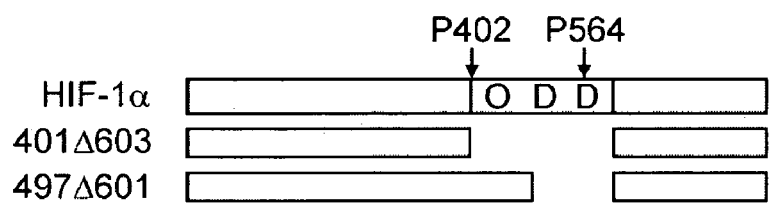
Figure 1C:
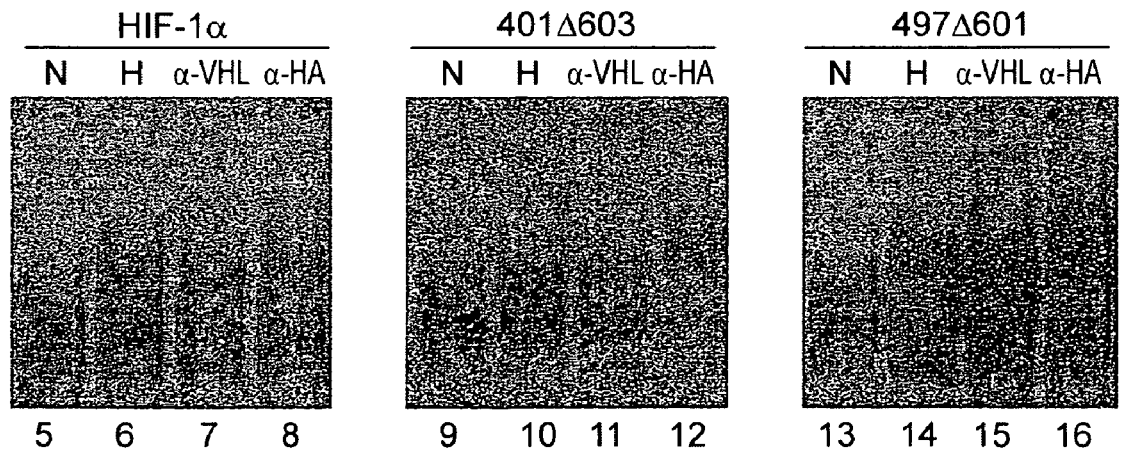
FIG. 1c, depicts gels of extracts from 293 cells transfected with the expression plasmids aforementioned were subjected to super-shift assays with the addition of anti-VHL and anti-hemagglutinin (α-HA) antibodies.

Previously, we proposed functional redundancy within the ODD because each part of the ODD independently confers degradation. In particular, removal of the C-terminal ODD that harbors Pro-564 led only to a more stable but not completely stable HIF-1α, suggesting additional mechanisms controlling HIF-1α degradation. To test whether VHL interacts with the N-terminal ODD, we transfected 293 cells with a plasmid expressing hemagglutinin (HA)-tagged HIF-1α that was wild-type, ODD entirely deleted from amino acids 401 to 603 (401Δ603), or ODD C-terminally deleted from amino acids 497 to 601 (497Δ601), as illustrated in FIG. 1b. VHL binding activity of the transfected HIF-1α was analyzed in super-shift assays. As expected, the addition of anti-VHL antibody shifted the slower migrating wild-type HIF-1 DNA-binding activity (FIG. 1c, lane 7). To differentiate the transfected HIF-1α from the endogenous, we also included in the assay an anti-HA antibody, which only super-shifted the DNA-binding complex resulting from transfected HIF-1α but retained the weak endogenous binding activity (compare lanes 6 and 8). When ODD-deleted HIF-1α was used, a constitutive HIF-1 binding pattern was observed (lanes 9 and 10), as shown in our previous reports (Huang, et al (1998) *Proc Natl Acad Sci USA* 95(14), 7987–92). However, no super-shift was observed with anti-VHL antibody (lane 11), whereas anti-HA antibody slowed the binding mobility (lane 12). This result is in agreement with the observation that VHL targets the ODD for HIF-1α degradation. In contrast, deletion of the C-terminal ODD retained a weaker yet noticeable super-shift by anti-VHL (lane 15), indicative of VHL binding to the N-terminal ODD. In keeping with this notion, HIF-1α (497Δ601) gave rise to an inducible rather than a constitutive binding pattern (compare lanes 13 and 14). This finding is also in good agreement with a recent report that hydroxylation of HIF-1α Pro-402 independently confers VHL binding (Masson, et al (2001) *Embo J* 20(18), 5197–206.). Thus, our results provide in vivo evidence that VHL interacts with the N-terminal as well as the C-terminal ODD for HIF-1α degradation.

Example 2

The ODD Contains a Core Region that is Stable and Transcriptionally Active

Figure 2A:
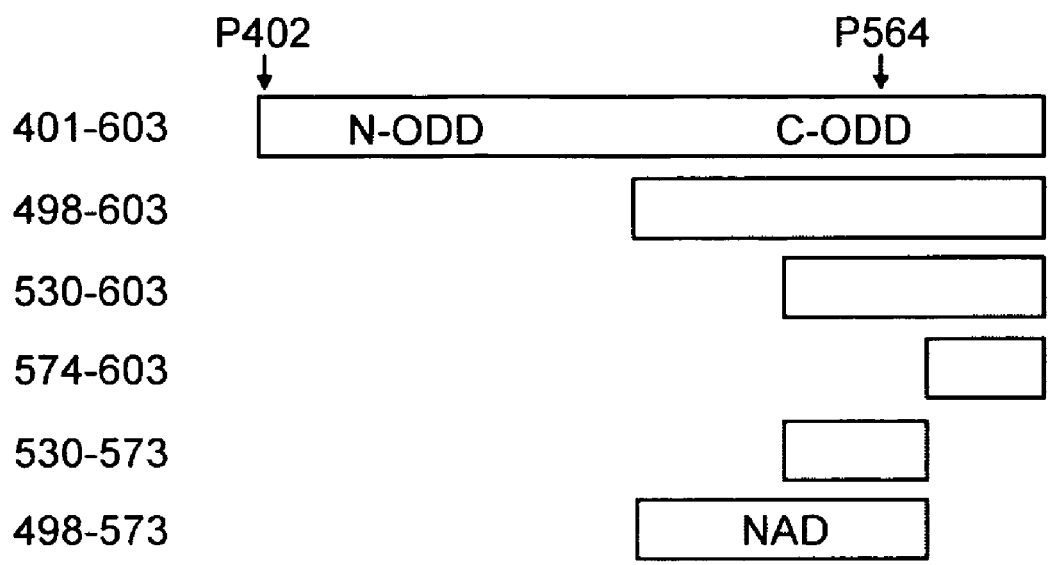
Figure 2B:
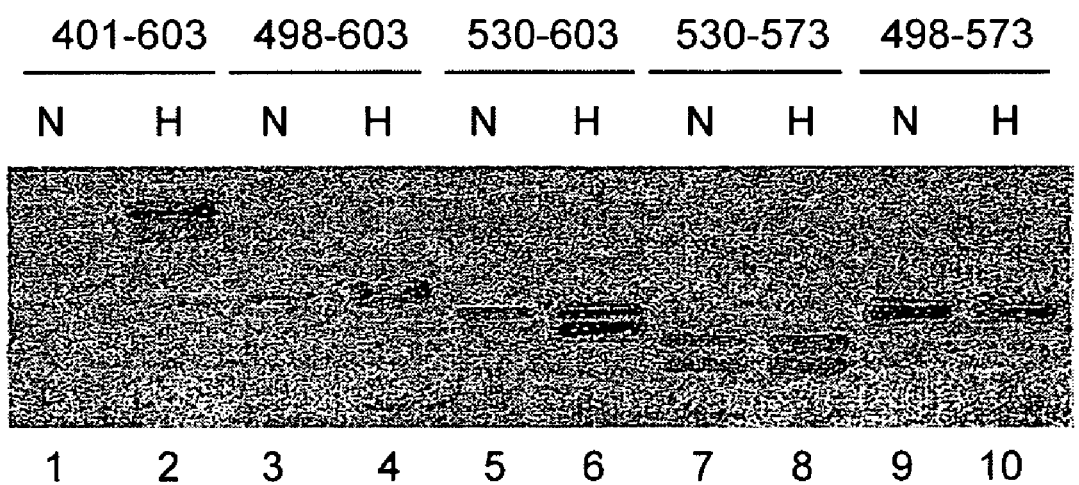
Figure 2C:
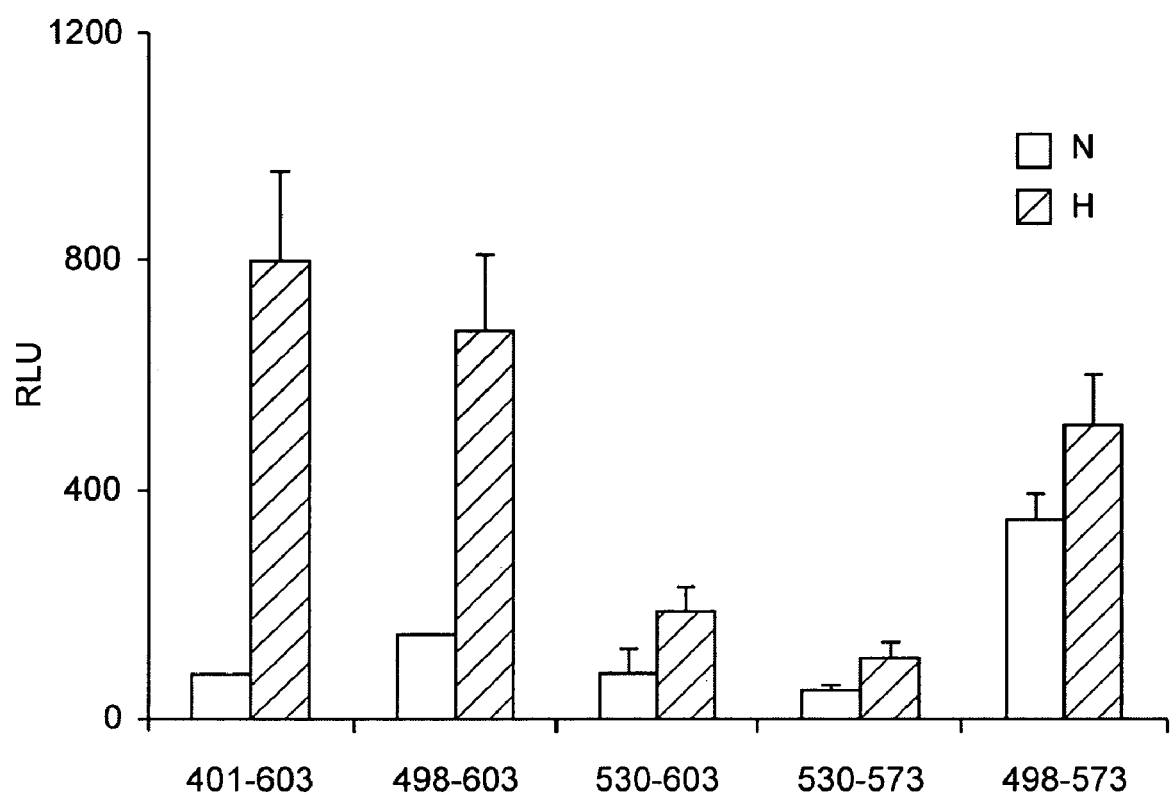
FIG. 2c represents a bar graph depicting transcriptional activity of the Gal4-ODD deletion under both normoxia and hypoxia.

To understand the structure and function of the ODD, we fused a Gal4 DNA-binding domain to various ODD mutants derived from serial N-terminal and C-terminal deletions, as schematized in FIG. 2a. Transfection of these mutants into 293 cells revealed that deletion of the N-terminal ODD resulted in increasing expression of Gal4-HIF1α(498–603) and Gal4-HIF1α(530–603) under normoxia (FIG. 2b, lanes 3 and 5), consistent with the notion of VHL binding to the N-terminus. However, deletion of amino acids 574–603 from the C-terminus significantly elevated normoxic expression levels of Gal4-HIF1α(530–573) and Gal4-HIF1α(498–573) (lanes 7 and 9), thereby abrogating hypoxic induction. In addition, Gal4-HIF1α(574–603) exhibited strong constitutive expression (data not shown). Interestingly, both Gal4-HIF1α(530–573) and Gal4-HIF1α(498–573) contain Pro-564, which is critical VHL binding through hydroxylation (28–30). Thus, our results suggest that in addition to Pro-564, the downstream sequence also contributes to oxygen-dependent proteolysis, please see FIG. 2 of inherent transcription al activity. However, Because part of the ODD overlaps an N-terminal activation domain (NAD) of HIF-1α (Jiang, et al (1997) *J Biol Chem* 272(31), 19253–60; Pugh, et al (1997) *J Biol Chem* 272(17), 11205–14; Ema, et al (1999) *Embo J* 18(7), 1905–14), we examined the functional role of these Gal4-HIF1α fusions in a Gal4 luciferase reporter system in order to establish a link between HIF-1α degradation and its transcriptional activity. Consistent with the protein levels mentioned previously, removal of the N-terminal ODD [Gal4-HIF1α(498–603)] slightly increased normoxic but modestly decreased hypoxic transcriptional activity (FIG. 2c). Further deletion from the N-terminus [Gal4-HIF1α(530–603)] resulted in significant loss of luciferase reporter activity, even though the protein was more stable, implying the requirement of amino acids 498 to 530 for transcriptional activity. Interestingly, Gal4-HIF1α(498–573), which was missing amino acids 574–603 but stable, exhibited a striking 2.4-fold increase in transcription under normoxia in comparison with Gal4-HIF1α(498–603), indicative both Gal4-HIF1α(498–530) (data not shown) and Gal4-HIF1α(530–573) alone showed much weaker activity. Therefore, we conclude that the core NAD lies within amino acids 498–573 of HIF-1α and is constitutively active. Transcriptional activity is registered as relative luciferase units (RLU), which were plotted as means plus standard errors from four experiments.

Example 3

Pro-564 is Necessary but Insufficient for VHL Binding

To investigate the molecular basis for the constitutive activity of HIF1α super-shift assays were performed to analyze in vivo VHL binding activity. As expected, transfection with Gal4-HIF1α(401–603) exhibited hypoxic induction of Gal4 DNA-binding activity (FIG. 3, lanes 1 and 2) and VHL binding activity (lane 5). The Gal4 binding activity was confirmed by the addition of excessive unlabeled Gal4 oligonucleotides and anti-Gal4 antibody respectively, resulting in abrogation or super-shift of the binding activity (lanes 3 and 4). Likewise, a super-shift by anti-VHL antibody was observed with Gal4-HIF1α(498–603) and Gal4-HIF1α(530–603) (lanes 8 and 12). However, we could not detect such mobility shift with Gal4-HIF1α(498–573) and Gal4-HIF1α(530–573) (lanes 10 and 14) when the C-terminus of ODD (amino acids 574–603) was deleted. Thus, these results suggest that stabilization of Gal4-HIF1α (498–573) and Gal4-HIF1α(530–573) was due to the loss of VHL binding, providing further evidence that, in addition to Pro-564, the downstream sequence is required for in vivo VHL binding, please see FIG. 3.

To further test this hypothesis, co-immunoprecipitation of in vitro translated Gal4-ODD fusions with VHL was performed. The Gal4-ODD deletion mutants and VHL were in vitro translated in the presence and absence of [$^{35}$S]methionine, respectively. The translated products were mixed together for co-immunoprecipitation with anti-VHL antibody. Input (10%) was shown in the upper panel. b, In vitro translated Gal4-HIF1α(530–603) was tested for the specificity of VHL binding by respective addition of anti-VHL (α-VHL) and anti-HA (α-HA) antibodies, or by respective omission of the VHL protein (–VHL) and antibody (–Ab). c, Pro-513, Pro-516, Pro-564, and Pro-567 in Gal4-HIF1α (401–603) were mutated to alanine individually or simultaneously (4P>4A). The mutants were examined subsequently for VHL binding. Input (10%) was shown in the upper panel.

Figure 4A:
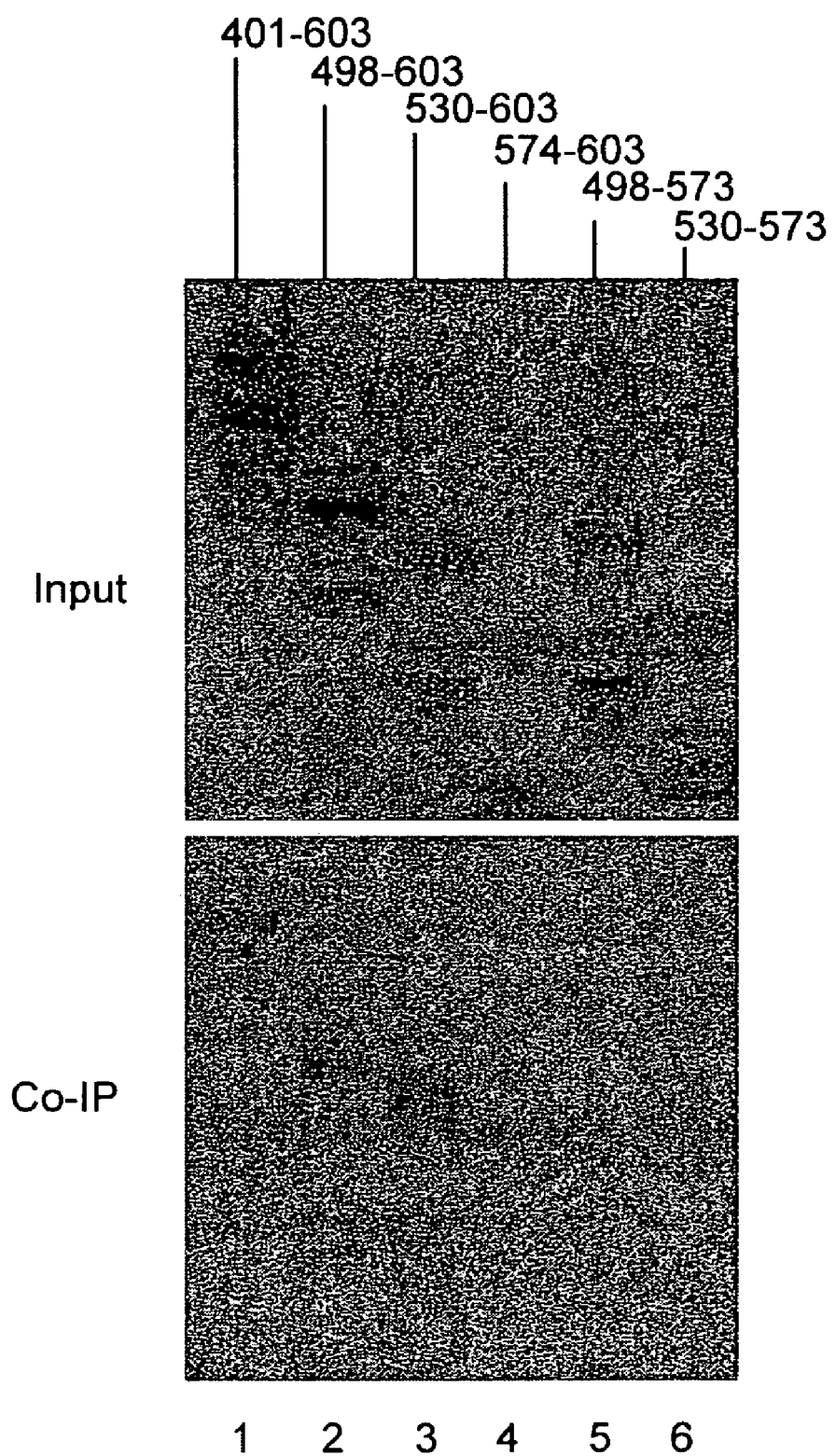
FIG. 4 depicts gels demonstrating Pro-564 of HIF-1α is necessary but not sufficient for VHL binding in vitro.

Consistently, Gal4-HIF1α(401–603), Gal4-HIF1α (498–603), and Gal4-HIF1α(530–603) were co-precipitated by anti-VHL antibody (FIG. 4a, lower panel, lanes 1–3). By contrast, Gal4 fusions lacking amino acids 574–603 [Gal4-HIF1α(498–573) and Gal4-HIF1α(530–573)] showed no interaction with VHL (lanes 5 and 6). In addition, Gal4-HIF1α(574–603) alone did not bind to VHL (lane 4), even though all the constructs were translated in vitro at similar levels (upper panel). Taken together, these results indicate the requirement of HIF-1α amino acids 530–603 for VHL binding, please see FIG. 4.

Figure 4B:
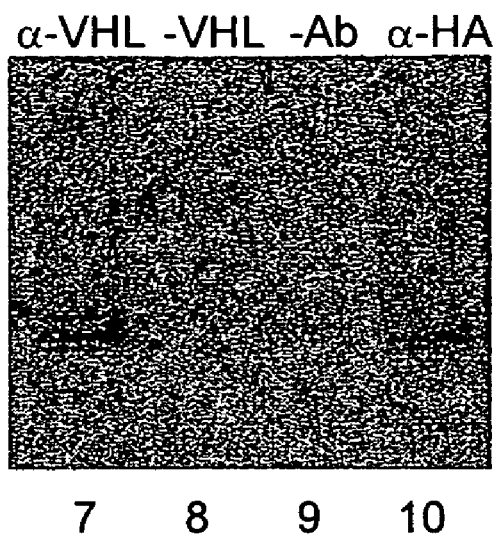
Figure 4C:
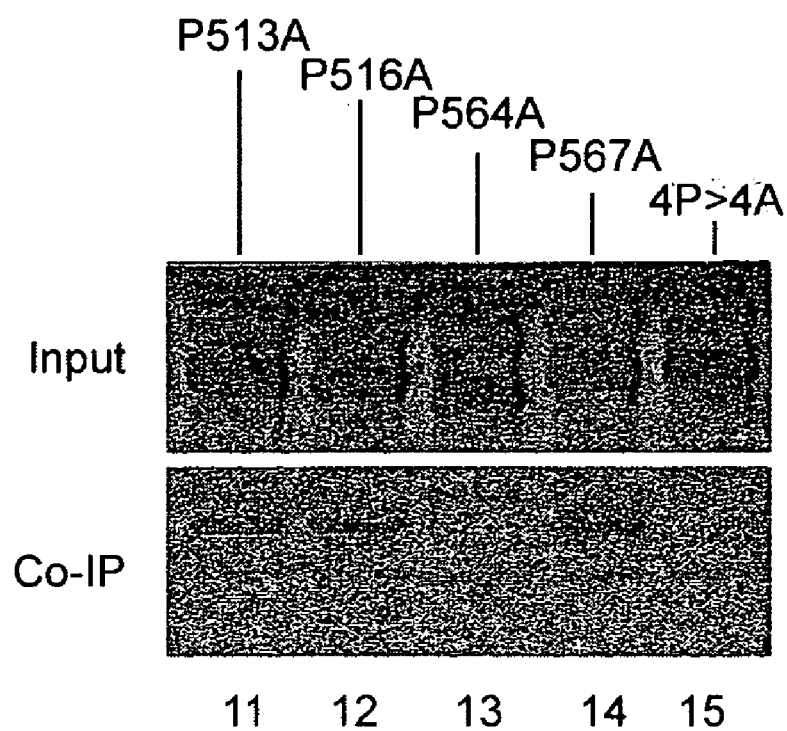

The interaction between VHL and Gal4-HIF1α(530–603) was further validated in FIG. 4b, in which no interaction was observed when in vitro translated VHL or anti-VHL antibody was omitted (FIG. 4b, lanes 8 and 9). Furthermore, because the VHL protein used contains an HA tag, the addition of anti-HA antibody also co-precipitated Gal4-HIF1α(530–603) (lane 10). To ensure the critical role of HIF-1α Pro-564 for VHL binding in our systems, we made an alanine substitution and, as expected, observed no VHL interaction (FIG. 4c, lane 13). In contrast, alanine substitutions of other proline residues within the ODD (Pro-513, Pro-516, and Pro-567) produced no effect, suggesting the specific requirement of Pro-564 for VHL binding, consistent with previous reports (Ivan, et al (2001) *Science* 292(5516), 464–8; JAAkkola, et al (2001) *Science* 292(5516), 468–72.; Yu, et al (2001) *Proc Natl Acad Sci USA* 98(17), 9630–5). Therefore, we conclude that VHL binding requires not only Pro-564 of HIF-1α but also the downstream sequence.

Example 4

Leu-574 is Required for VHL-Mediated Degradation

To further examine the molecular determinants of VHL binding, we asked whether Leu-574 could be involved because this residue is highly conserved and included in all the studies of HIF-1α oligopeptide binding to VHL (28,29). To that end, Gal4-HIF1α(498–574) was constructed and analyzed for in vitro VHL binding., In vitro translated Gal4-HIF1α(498–573), Gal4-HIF1α(498–574), Gal4-HIF1α(498–573)L574S, Gal4-HIF1α(498–603), and Gal4-HIF1α(498–603)L574S were mixed with VHL and co-immunoprecipitated by anti-VHL antibody for VHL binding activity. Input (10%) was shown in the upper panel. b and c, These Gal4 fusion constructs were transfected into 293 cells for analyzing their protein levels by Western blot, or transfected into Hep3B cells for examining their transcriptional activity in a Gal4 reporter system. Transcriptional activity is registered as relative luciferase units (RLU), which were plotted as means plus standard errors from four experiments.

Figure 5A:
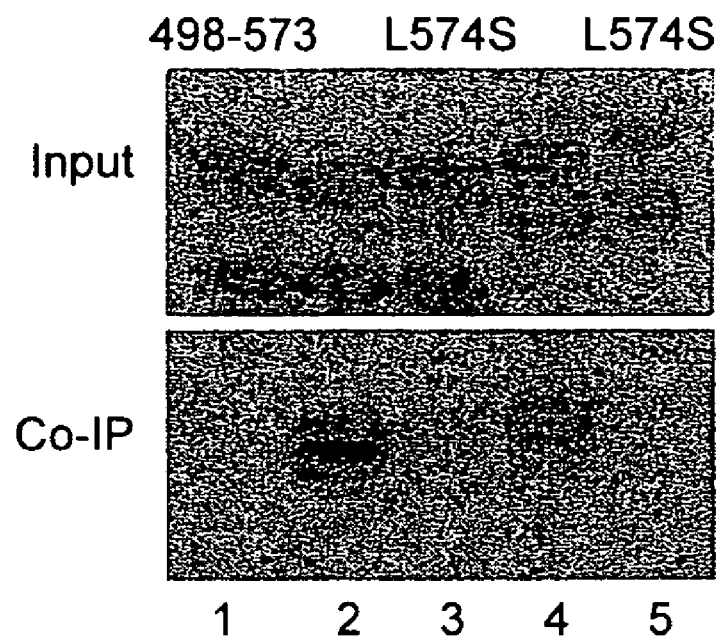
FIG. 5 depicts gels and data illustrating the inclusion of Leu-574 renders HIF-1α unstable under normoxia.

Remarkably, addition of a single leucine residue to Gal4-HIF1α(498–573) gained VHL binding (FIG. 5a, lanes 1 and 2), whereas mutation of Leu-574 to serine abolished the binding (lane 3), indicating an essential role for Leu-574 in VHL binding. To corroborate the importance of Leu-574, we also mutated Leu-574 in Gal4-HIF1α(498–603) and asked whether substitution with serine would affect VHL binding. Consistently, the mutation resulted in loss of VHL binding (compare lanes 4 and 5). Thus, these results provide compelling evidence that Leu-574 is critically involved in VHL binding, please see FIG. 5.

Figure 5B:
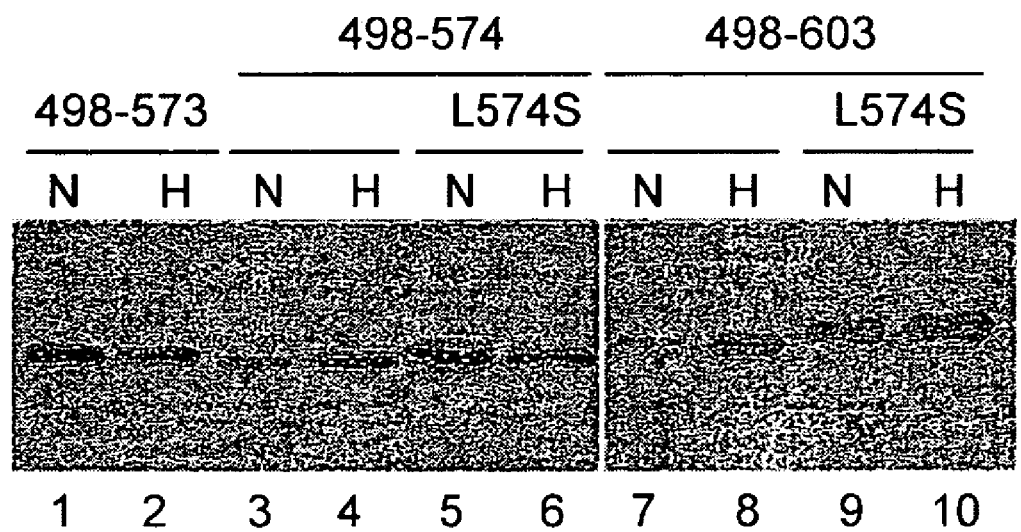
Figure 5C:
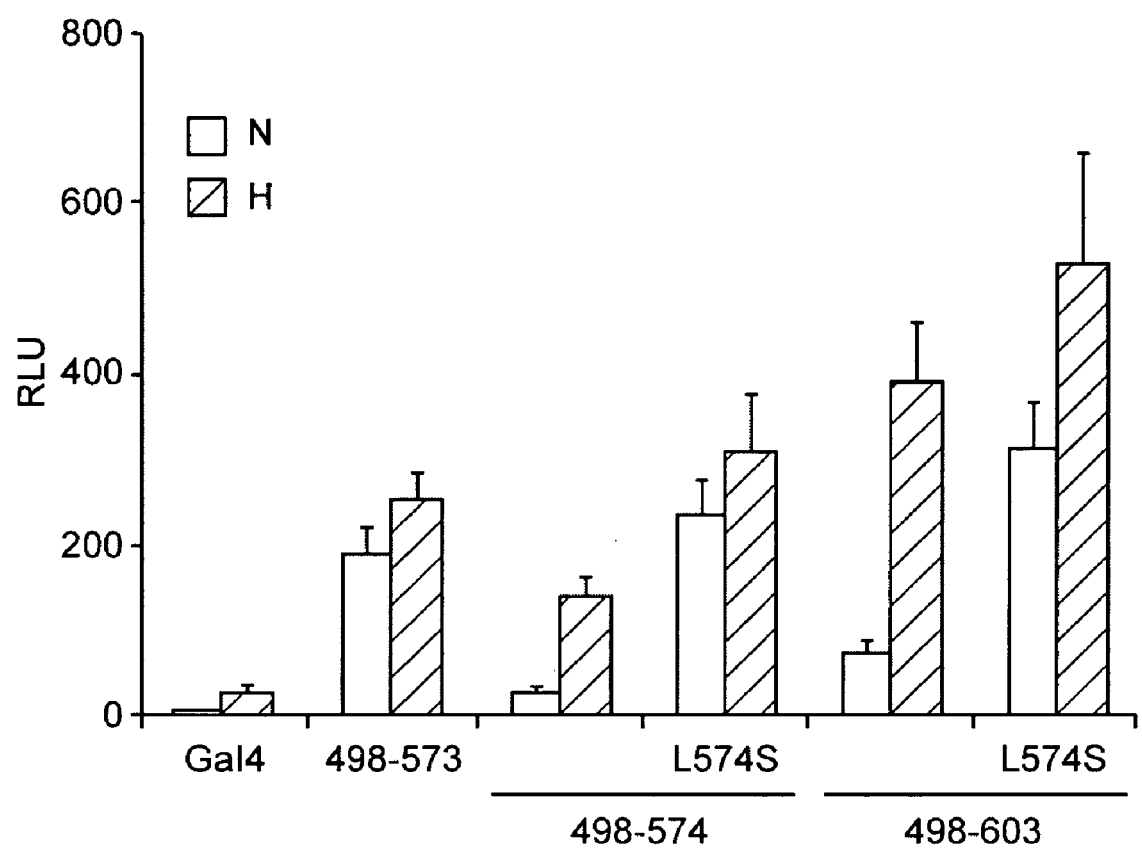

To address the role of Leu-574 in protein stability, we examined expression levels of these constructs by Western blot analysis. In comparison to Gal4-HIF1α(498–573), Gal4-HIF1α(498–574) exhibited an approximately 3-fold decrease in protein levels under normoxia (FIG. 5b, compare lanes 1 and 3), supporting the role of Leu-574 in VHL-mediated degradation. Consistently, mutation of Leu-574 prevented the degradation process, resulting in a stable Gal4-HIF1α(498–574) (compare lanes 3 and 5). Furthermore, mutation of Leu-574 gave rise to a 7-fold increase in the expression level of Gal4-HIF1α(498–603) (compare lanes 7 and 9). Taken together, these results demonstrate that Leu-574 plays a critical role in the VHL degradation pathway, although additional residues between amino acids 575–603 may also contribute oxygen-dependent degradation of the C-terminal ODD.

As shown above, the core NAD lies within amino acids 498–573 of HIF-1α. To examine the effect of Leu-574 on transcriptional activity, we employed the Gal4 luciferase reporter system aforementioned. As expected, addition of Leu-574 significantly lowered the luciferase reporter activity (FIG. 5c), by 6.5-fold under normoxia. In contrast, Gal4-HIF1α(498–574)L574S gave rise to a similar reporter activity as that of Gal4-HIF1α(498–573), supporting the involvement of Leu-574 in ODD instability. Furthermore, under oxygenated conditions, Gal4-HIF1α(498–603)L574S exhibited a 4.3-fold increase in luciferase activity than the wild-type. Therefore, these results provide further evidence that Leu-574 plays a critical role in VHL mediated degradation of HIF-1α, thereby regulating HIF-1α transcriptional activity.

Example 5

Leu-574 is Required for HIF-1α Instability

As reported previously, mutation or deletion of Leu-574 in HIF-1α gave rise to the stabilization of C-ODD (amino acids 498–603), resulting from loss of VHL binding (32). To confirm the destabilizing nature of Leu-574, Leu-574 was substituted with serine (L574S) in full-length HIF-1α. It has been shown previously that both Pro-402 and Pro-564 are independently recognized by the VHL ubiquitin ligase (Masson, N., Willam, C., Maxwell, P. H., Pugh, C. W., and Ratcliffe, P. J. (2001) Independent function of two destruction domains in hypoxia-inducible factor-alpha chains activated by prolyl hydroxylation. *Embo J* 20, 5197–5206.), consistent with the hypothesis of functional redundancy within the ODD (Huang, L. E., Gu, J., Schau, M., and Bunn, H. F. (1998) Regulation of hypoxia-inducible factor 1alpha is mediated by an O2-dependent degradation domain via the ubiquitin-proteasome pathway. *Proc Natl Acad Sci USA* 95, 7987–7992). Therefore, mutation of Pro-402 only modestly increased HIF-1α levels in normoxia (Pereira, T., Zheng, X., Ruas, J. L., Tanimoto, K., and Poellinger, L. (2003) Identification of residues critical for regulation of protein stability and the transactivation function of the hypoxia-inducible factor-1 alpha by the von Hippel-Lindau tumor suppressor gene product. *J Biol Chem* 278, 6816–6823) (FIG. 1A, compare lanes 1 and 3). Similar to a single Pro-564 mutation in full-length HIF-1α (data not shown), mutation of Leu-574 alone hardly affected HIF-1α expression. It is noteworthy that the use of greater amount of plasmids gave rise to constitutive expression of wild-type HIF-1α (data not shown), presumably due to the saturation of the proteasome system. Therefore, the above result suggests that the transfection conditions were appropriate, even though single mutation of Pro-402, Pro-564, or Leu-574 did not stabilize HIF-1α in normoxia, consistent with our previous finding. However, mutations of both Leu-574 and Pro-402 significantly enhanced HIF-1α stability in normoxia, resulting in constitutive expression of the protein and significant reduction of the inducibility by desferrioxamine (DFO), an iron chelator (lanes 5 and 6). Similar expression pattern was observed when both Pro-402 and Pro-564 were mutated (lanes 7 and 8), consistent with a previous report (Pereira, T., Zheng, X., Ruas, J. L., Tanimoto, K., and Poellinger, L. (2003) Identification of residues critical for regulation of protein stability and the transactivation function of the hypoxia-inducible factor-1 alpha by the von Hippel-Lindau tumor suppressor gene product. *J Biol Chem* 278, 6816–6823). These results indicate that Leu-574 participates in the same pathway as Pro-564 for HIF-1α degradation.

As HIF-1α transcriptional activity depends on its stability, the role of Leu-574 in HIF-1α degradation was further examined in a HIF-1 mediated reporter system (Huang, L. E., Arany, Z., Livingston, D. M., and Bunn, H. F. (1996) Activation of hypoxia-inducible transcription factor depends primarily upon redox-sensitive stabilization of its alpha subunit. *J Biol Chem* 271, 32253–32259). Similar to the Pro-402 and Pro-564 double mutant, the Pro-402 and Leu-574 double mutant exhibited a significant increase in transcriptional activity in 293 cells, especially under normoxia (FIG. 1B). It is noteworthy that the transcriptional activity of both mutants remained hypoxia-inducible, despite similar protein levels between normoxic and hypoxic samples. This discrepancy may be accounted for by the fact HIF-1 inhibits the transcriptional activity of HIF-1α in normoxia, whereas endogenous HIF-1α, in addition to exogenously expressed HIF-1α mutants, enhances the reporter activity only in hypoxia, thereby maintaining transcriptional inducibility. Similar results were obtained in Hep3B cells (data not shown). In addition, mutation of Leu-574 alone also elevated the reporter activity. These findings, together with our previous report (Huang, L. E., Pete, E. A., Schau, M., Milligan, J., and Gu, J. (2002) Leu-574 of HIF-1alpha is essential for the von Hippel-Lindau (VHL)-mediated degradation pathway. *J Biol Chem* 277, 41750–41755), support that Leu-574 of HIF-1α is required for C-ODD proteolysis by facilitating VHL binding, thereby resulting in HIF-1α degradation.

Example 6

Mutation of Leu-574 Inhibits Prolyl Hydroxylation

To understand the mechanism underlying the role of Leu-574 in VHL-mediated degradation, experiments were focused on how Leu-574 controls VHL binding. Recent structural studies on VHL-HIF-1α interaction indicate that Hyp-564 of HIF-1α is strictly required for VHL recognition, whereas the neighboring amino acid residues only contribute to the complex's stability through a β sheet-like contact.

(Hon, W. C., Wilson, M. I., Harlos, K., Claridge, T. D., Schofield, C. J., Pugh, C. W., Maxwell, P. H., Ratcliffe, P. J., Stuart, D. I., and Jones, E. Y. (2002) Structural basis for the recognition of hydroxyproline in HIF-1 alpha by pVHL. *Nature* 417, 975–978;

Min, J. H., Yang, H., Ivan, M., Gertler, F., Kaelin, W. G., Jr., and Pavletich, N. P. (2002) Structure of an HIF-1alpha -pVHL complex: hydroxyproline recognition in signaling. *Science* 296, 1886–1889.). Furthermore, these studies showed that Leu-574 is nonessential when Pro-564 is artificially hydroxylated, suggesting the involvement of Leu-574 in the upstream event(s), such as prolyl hydroxylation. To test this hypothesis, polyclonal rabbit antisera was raised against a synthetic peptide corresponding to amino acids 558–569 of HIF-1α in which Pro-564 is hydroxylated, and termed the resultant antibody as anti-Hyp-564.

To test the epitope specificity of the antibody, full-length HIF-1α was transfected and its Pro-402 and Pro-564 mutants into 293 cells (containing low levels of endogenous HIF-1α) in the presence of a proteasome inhibitor Cbz-LLL. As shown in FIG. 2A, anti-Hyp-564 detected HIF-1α wild-type and the Pro-402 mutant, but not those containing mutated Pro-564 (top panel), indicating the requirement of Pro-564 for the epitope. In contrast, an anti-HIF-1α antibody (recognizing HIF-1α amino acids 610–727) revealed all the HIF-1α variants (bottom panel). To demonstrate the antibody specificity for recognizing hydroxylated Pro-564, to an in vitro translation system was used in which either DFO or $FeCl_2$ was added to generate non-hydroxylated or hydroxylated HIF-1α (Ivan, M., Kondo, K., Yang, H., Kim, W., Valiando, J., Ohh, M., Salic, A., Asara, J. M., Lane, W. S., and Kaelin, W. G., Jr. (2001) HIFalpha targeted for VHL-mediated destruction by proline hydroxylation: implications for O2 sensing. *Science* 292, 464–468; Jaakkola, P., Mole, D. R., Tian, Y. M., Wilson, M. I., Gielbert, J., Gaskell, S. J., Kriegsheim, A., Hebestreit, H. F., Mukherji, M., Schofield, C. J., Maxwell, P. H., Pugh, C. W., and Ratcliffe, P. J. (2001) Targeting of HIF-alpha to the von Hippel-Lindau ubiquitylation complex by O2-regulated prolyl hydroxylation. *Science* 292, 468–472.). The anti-Hyp-564 antibody showed strong specificity to the hydroxylated form (FIG. 2B, top two panels), in contrast to the equal recognition of both HIF-1α forms by the anti-HIF-1α antibody (bottom panel). In addition, the recognition of Hyp-564 by the anti-Hyp-564 was proportional to the increasing amount of hydroxylated HIF-1α.

Consistent with the fact that HIF-1α is hydroxylated in normoxia, the anti-Hyp-564 detected the hydroxylated form primarily in normoxic 293 cell extracts (FIG. 2C, top panel). In contrast, anti-HIF-1α antibody showed HIF-1α expression predominantly in hypoxic cell extracts (bottom panel). In keeping with the hypothesis that Leu-574 is involved in prolyl hydroxylation, mutation of Leu-574 markedly reduced hydroxylated HIF-1α levels in normoxia. It is noteworthy that the multiple bands detected by anti-Hyp-564 were conspicuous particularly in normoxia (FIG. 2C), but became less significant when the proteasomal degradation was inhibited by Cbz-LLL or hypoxia (FIGS. 2A, 2C) or in the in vitro system (FIG. 2B), indicative of partially degraded HIF-1α. To determine the hydroxylated form in reference to the total amount of HIF-1α, the signals by densitometry were quantified and the ratio of the two in arbitrary numbers presented (FIG. 2D). In comparison to normoxia, DFO treatment reduced prolyl hydroxylation by ~90% in wild-type HIF-1α. A similar reduction of the ratio was observed with the L574S mutant expressed in normoxia, while DFO treatment resulted in a further decrease. These results provide evidence that Leu-574 is involved in Pro-564 hydroxylation. To corroborate this finding, the hydroxylation status of the wild-type HIF-1α with the L574S mutant was compared in the presence of Cbz-LLL. The ratio of hydroxylated Pro-564 of Leu-574 mutant under normoxia was only one fifth of that of the wild-type HIF-1α (data not shown). Taken together, these data support that mutation of Leu-574 affects Pro-564 hydroxylation.

Figures 3A, 3B, 3C:
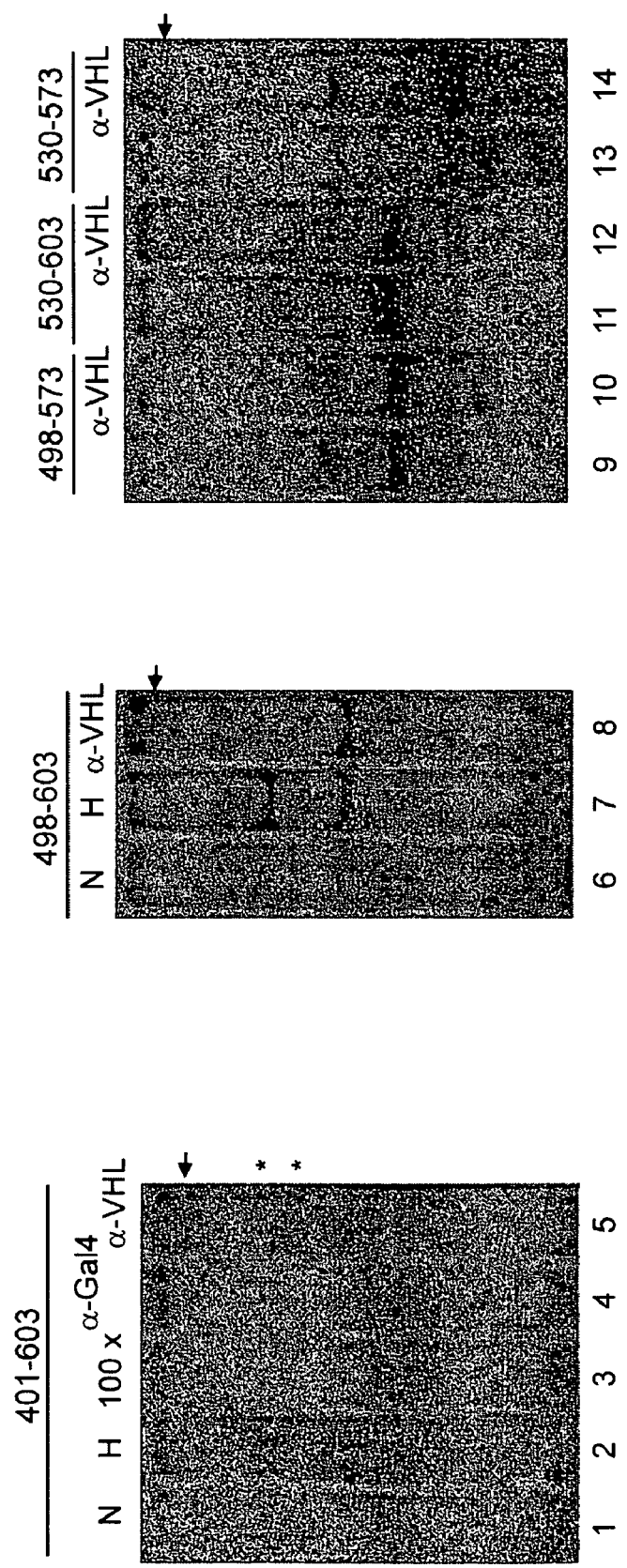
FIG. 3a illustrates binding of anti-VHL antibody in Gal4-HIF 1α(401Δ603) expressed in 293 cells as analyzed in an electrophoretic mobility shift assay; and wherein FIGS. 3b and c, Gal4-ODD deletion mutants containing Leu-574 bind anti-VHL antibody and mutants not containing Leu-574 do not.

To further test this hypothesis, the role of Leu-574 in prolyl hydroxylation with C-ODD was analyzed (in the absence of Pro-402). Both C-ODD and its L574S mutant in Gal4 fusions were transfected in 293 cells and assayed for prolyl hydroxylation. Whereas DFO significantly diminished the ratio of hydroxylated form of Gal4-C-ODD, mutation of Leu-574 further decreased the ratio in normoxia and iron chelation (FIGS. 3A and B). Previously, we showed that deletion of C-ODD from the C-terminal (amino acids 574–603) rendered the protein more stable than mutation of Leu-574 alone (Huang, L. E., Pete, E. A., Schau, M., Milligan, J., and Gu, J. (2002) Leu-574 of HIF-1 alpha is essential for the von Hippel-Lindau (VHL)-mediated degradation pathway. *J Biol Chem* 277, 41750–41755), suggesting the involvement of the deleted region in protein degradation. Such a deletion mutant (amino acids 498–573) ablated hydroxylation, in contrast to another deletion mutant (amino acids 498–574) that contains Leu-574 (FIG. 3c). Therefore, Leu-574 of HIF-1α is essential for prolyl hydroxylation, although residues 575–603 may also participate in the process.

Example 7

The Spacing Between Pro-564 and Leu-574 Affects HIF-1α Stability and Transcriptional Activity To understand how Leu-574 is engaged in prolyl hydroxylation, the spacing between the two residues was analyzed. Positional shift of Leu-574 in reference to Pro-564 was engineered by altering the intermediate region that has minimal contact with VHL (Hon, W. C., Wilson, M. I., Harlos, K., Claridge, T. D., Schofield, C. J., Pugh, C. W., Maxwell, P. H., Ratcliffe, P. J., Stuart, D. I., and Jones, E. Y. (2002) Structural basis for the recognition of hydroxyproline in HIF-1 alpha by pVHL. *Nature* 417, 975–978; Min, J. H., Yang, H., Ivan, M., Gertler, F., Kaelin, W. G., Jr., and Pavletich, N. P. (2002) Structure of an HIF-1 alpha -pVHL complex: hydroxyproline recognition in signaling. *Science* 296, 1886–1889.); an aspartate was either deleted or inserted at Asp-570 in Gal4-C-ODD (FIG. 4A). Unlike the L574S mutation, deletion of Asp-570 decreased levels of C-ODD expression in 293 cells under normoxic and hypoxic conditions, and the insertion resulted in an even greater reduction (FIG. 4B). In contrast to the protein levels, these mutants displayed an enhanced ratio of the hydroxylated form in normoxia, most significantly with the insertion mutant (FIGS. 4C and D), presumably accounting for the elevated instability. Accordingly, both the deletion and insertion mutants maintained VHL binding activity (FIGS. 4E and 4F). It is noteworthy that VHL binding was abolished with mutation of Leu-574, but only diminished with mutation of Leu-562, a residue previously shown to be critical for Pro-564 hydroxylation (Ivan, M., Kondo, K., Yang, H., Kim, W., Valiando, J., Ohh, M., Salic, A., Asara, J. M., Lane, W. S., and Kaelin, W. G., Jr. (2001) HIFalpha targeted for VHL-mediated destruction by proline hydroxylation: implications for O2 sensing. *Science* 292, 464–468.). Identical VHL binding results were obtained when the deletion and insertion mutants were analyzed in the context of C-terminally deleted C-ODD (amino acids 498–574, data not shown). Taken together, these results suggest that the nine-residue spacing between Pro-564 and Leu-574 is not obligatory, but stimulatory if altered, for prolyl hydroxylation.

As C-ODD contains an N-terminal activation domain of HIF-1α, effects of these mutations were tested on transcriptional activity in a Gal4-mediated reporter system (Huang, L. E., Pete, E. A., Schau, M., Milligan, J., and Gu, J. (2002) Leu-574 of HIF-1 alpha is essential for the von Hippel-Lindau (VHL)-mediated degradation pathway. *J Biol Chem* 277, 41750–41755). Interestingly, although the insertion of aspartate markedly reduced C-ODD expression, this mutant exhibited enhanced transcriptional activity (FIG. 5). In contrast, the deletion mutation lowered transcriptional activity. These results suggest that the spacing between Pro-564 and Leu-574 or Asp-570 itself contributes to the transcriptional activity of the N-terminal activation domain.

Example 8

Leu-574 of HIF-1α is Required for PHD2/HPH2 Binding

Figure 6A:
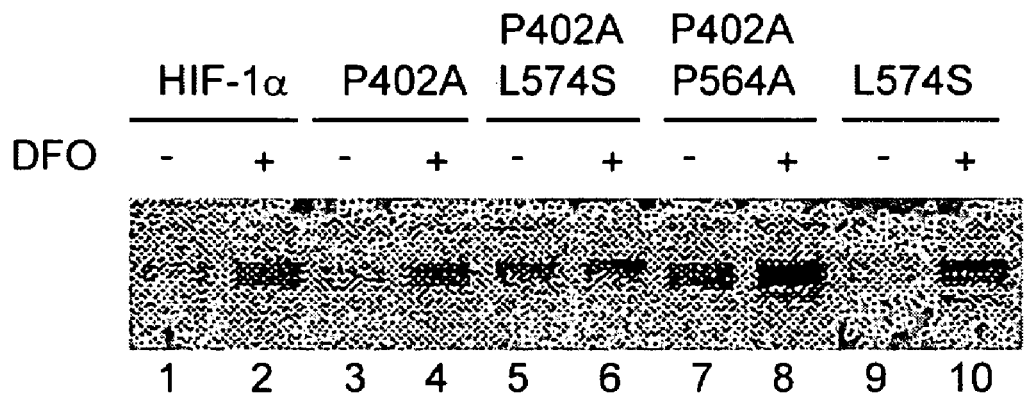
FIG. 6 illustrates the role of Leu-574 in normoxic degradation of full-length HIF-1α. wherein A) wild-type HIF-1α and its mutants, as indicated, were transiently expressed in 293 cells; after 4-h DFO treatment, expression levels of HIF-1α variants were examined by anti-HA immunoprecipitations, followed by Western blot with anti-HIF-1α antibodies; B) transcriptional activity of these HIF-1α variants under normoxia (N) and hypoxia (H) were determined by luciferase reporter assays in Hep3B cells; relative luciferase units (RLU) were plotted as means plus standard errors from three independent experiments in duplicates.
Figure 6B:
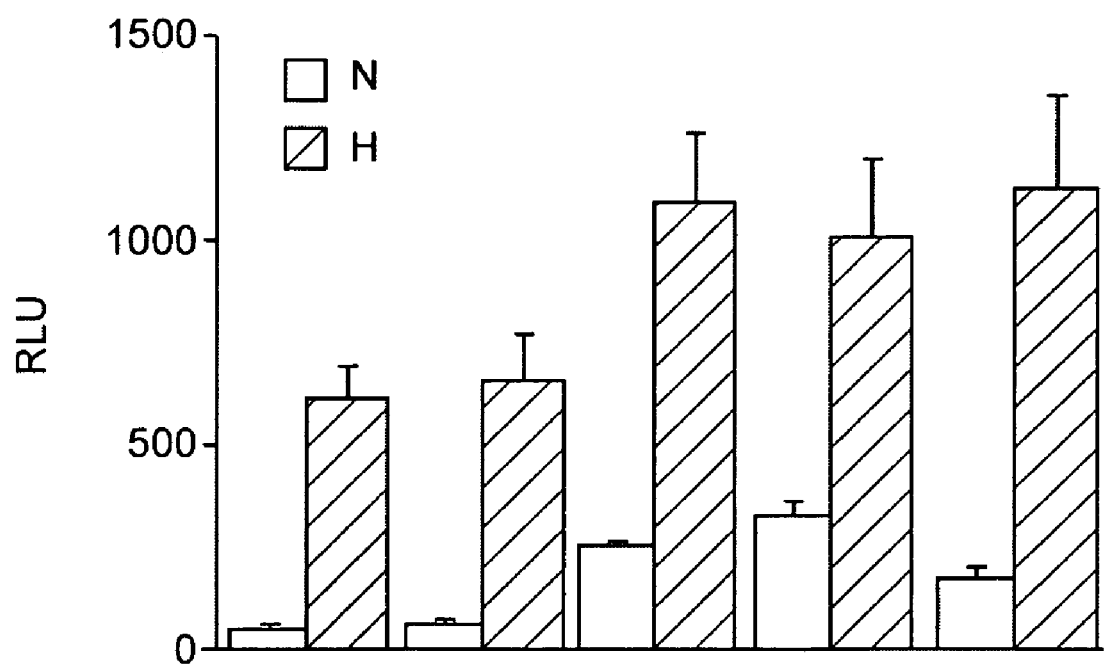
Figure 8C:
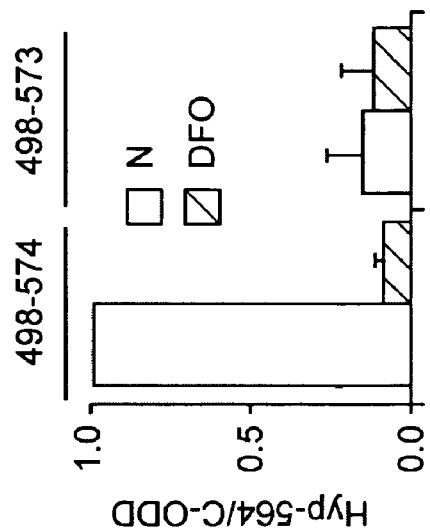
FIG. 8 illustrates that Leu-574 is required for Pro-564 hydroxylation wherein A,B) role of Leu-574 in prolyl hydroxylation was investigated in Gal4-C-ODD as in FIGS. 2B and 2C; the signal intensity is specified at the bottom of each lane; the results in B were obtained from 3 independent experiments; C) prolyl hydroxylation was further determined in C-ODD with deletions from the C terminus (498–574 and 498–573), and presented in a ratio of Hyp-564/C-ODD from 3 independent experiments.
Figure 8B:
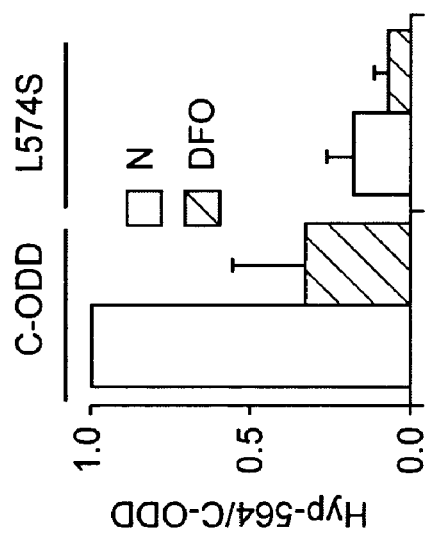
Figure 8A:
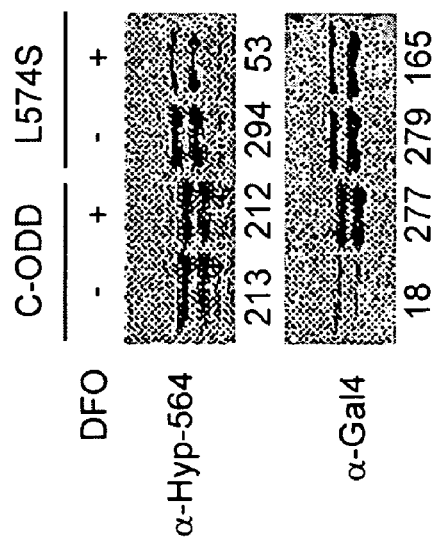
Figure 9E:
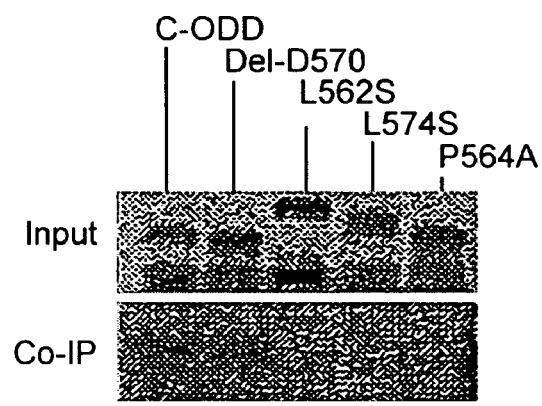
FIG. 9 illustrates that positional changes of Leu-574 alter C-ODD hydroxylation and stability wherein A) sequence alignment of amino acids 556 to 575 of C-ODD and its mutants, including deletion (Del-D570) or insertion (Ins-D570) of an aspartate at Asp-570, and substitution of Leu-574 with serine (L574S); Pro-564 and Leu-574 are marked with shadows. B) Gal4-C-ODD and the mutants were examined for their expression levels as above; co-transfected yellow fluorescence protein (YFP) served as an internal control; C, D) the hydroxylation status of C-ODD and its mutants was determined as in FIG. 2; E, F) in vitro translated C-ODD and its mutants, as indicated, were assayed for VHL binding; one-fifth of the translated products were used as Input, and co-immunoprecipitated products were labeled as Co-IP.
Figure 9F:
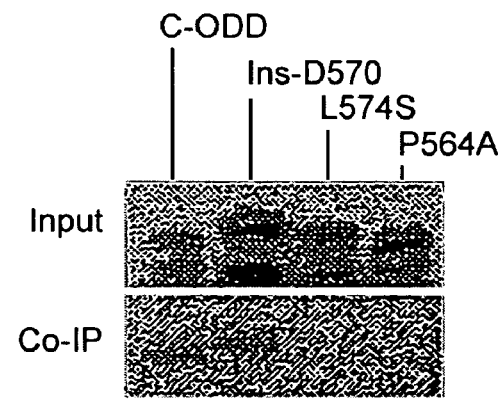
Figure 10:
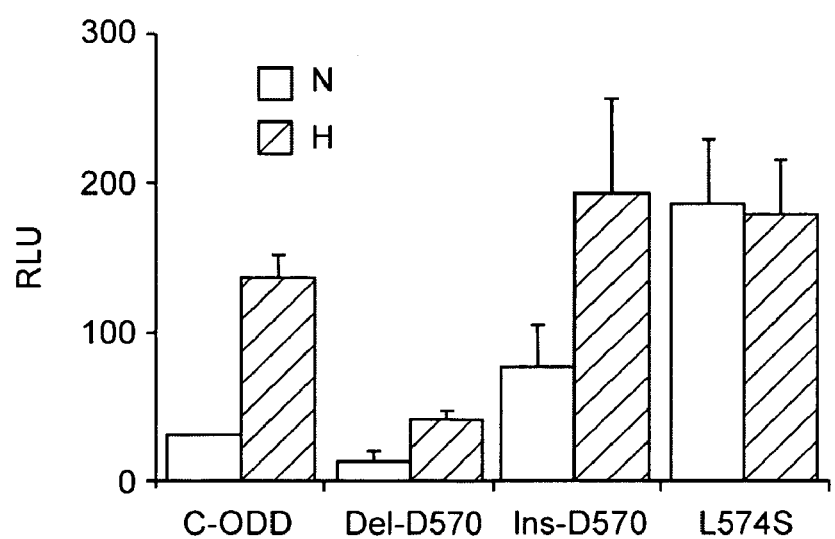
FIG. 10 illustrates that deletion or insertion of an aspartate at Asp-570 modulates NAD transcriptional activity wherein Gal 4-C-ODD and its mutants, as indicated, were tested for their transcriptional activity in Hep3B cells in a Gal4 reporter system (Hewitson, K. S., McNeill, L. A., Riordan, M. V., Tian, Y. M., Bullock, A. N., Welford, R. W., Elkins, J. M., Oldham, N. J., Bhattacharya, S., Gleadle, J. M., Ratcliffe, P. J., Pugh, C. W., and Schofield, C. J. (2002) Hypoxia inducible factor (HIF) asparagine hydroxylase is identical to factor inhibiting HIF (FIH) and is related to the cupin structural family. *J Biol Chem* 277, 26351–26355); cells in the absence or presence of hypoxic treatment were lysed and assayed for luciferase activity; relative luciferase units (RLU) were plotted as means plus standard errors from three independent experiments in duplicates.
Figure 11:
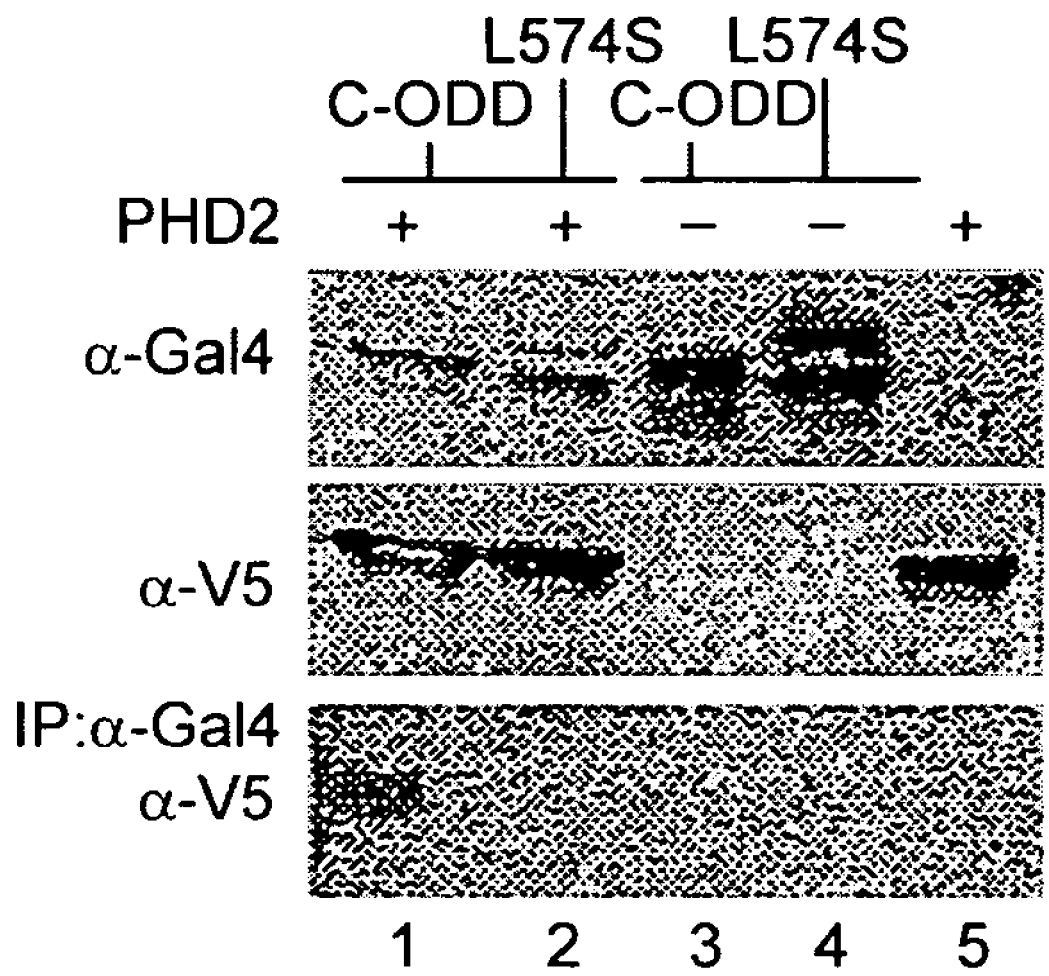
FIG. 11 illustrates that Leu-574 of HIF-1α is required for PHD2/HPH2 binding wherein Gal4-C-ODD and the L574S mutant were transfected into 293 cells in the presence or absence of V5-tagged PHD2/HPH2; after Cbz-LLL treatment, C-ODD-PHD2/HPH2 interaction was revealed by co-immunoprecipitation with anti-Gal4 antibodies, followed by Western blotting with anti-V5 antibodies (bottom); expression levels of Gal4 fusions and V5-tagged PHD2/HPH2 were determined in the upper and middle panels with indicated antibodies.

The role of Leu-574 in prolyl hydroxylation led to the question of whether the leucine is involved in the interaction with the HIF prolyl-4-hydroxylases that modify Pro-564. To that end, we performed co-immunoprecipitations of C-ODD with the HIF prolyl hydroxylases. FIG. 6 showed that in the presence of Cbz-LLL, PHD2/HPH2 was co-precipitated with C-ODD only when both were ectopically expressed in 293 cells (lanes 1, 3, 5). Furthermore, no co-precipitation was detected when Leu-574 was mutated, indicating the requirement of Leu-574 for PHD2/HPH2 interaction. It is noteworthy that the higher levels of Gal4 fusions in the absence of ectopically expressed PHD2/HPH2 (top and middle panels) support the specificity of co-immunoprecipitated PHD2/HPH2. Possible interactions of C-ODD with PHD1/HPH3 or PHD3/HPH1 were also examined, but failed to detect similar interaction under the same conditions (data not shown). Taken together, these data indicate that Leu-574 participates in the recruitment of PHD2/HPH2 for the subsequent hydroxylation of Pro-564

I claim:

1. The isolated hypoxia-inducible factor 1-alpha (HIF-1α) polypeptide of the sequence according to SEQ ID NO: 2 wherein Phe-Gln-X are present at amino acid residues 572–574 and X does not consist of Leu at position 574 and all other amino acid residues are unchanged.

2. The isolated HIF-1α polypeptide of the sequence according to SEQ ID NO: 2, wherein amino acid 574 consists of any amino acid other than leucine and all other amino acid residues are unchanged.

3. The isolated HIF-1α polypeptide of claim 2 wherein amino acid residue 574 consists of serine.

4. The isolated HIF-1α polypeptide of the sequence according to SEQ ID NO: 2, wherein amino acid 574 consists any amino acid other than leucine and amino acid 564 consist of any amino acid other than proline.

5. The isolated HIF-1α polypeptide of the sequence according to SEQ ID NO: 2, wherein amino acid 574 consists any amino acid other than leucine and amino acid 402 consist of any amino acid other than proline.

6. The isolated HIF-1α polypeptide of the sequence according to SEQ ID NO: 2, wherein amino acid 574 consists any amino acid other than leucine and amino acids 564 and 402 consist of any amino acid other than prolines.

7. The isolated HIF-1α polypeptide of the sequence according to SEQ ID NO: 2, wherein the leucine residue at position 574 is deleted from the polypeptide with the resulting polypeptide consisting of 825 amino acids.

8. The isolated HIF-1α polypeptide of the sequence according to SEQ ID NO: 2, wherein the leucine residue at position 574 is deleted from the polypeptide and the amino acid at position 564 consists of any amino acid other than proline with the resulting polypeptide consisting of 825 amino acids.

9. The isolated HIF-1α polypeptide of the sequence according to SEQ ID NO: 2, wherein the leucine residue at position 574 is deleted from the polypeptide and the amino acid at position 402 consists of any amino acid other than proline with the resulting polypeptide consisting of 825 amino acids.

10. The isolated HIF-1α polypeptide of the sequence according to SEQ ID NO: 2, wherein the leucine residue at position 574 is deleted from the polypeptide and the amino acid at positions 564 and 402 consist of any amino acid other than prolines with the resulting polypeptide consisting of 825 amino acids.

11. A composition comprising the isolated polypeptide according to any of claims 1–10 and a pharmaceutically acceptable carrier.

12. An isolated biologically active fragment of the HIF-1α polypeptide according to the amino acid sequence of SEQ ID NO: 2 wherein the active fragment contains amino acid residues from position 402 through 574 of SEQ ID NO: 2, wherein amino acid residue 574 consists of any amino acid other than Leu.

13. Isolated biologically active fragments of the HIF-1α polypeptide according to the amino acid sequence of SEQ ID NO: 2 wherein the active fragment contains amino acid residues from position 402 through 574 of SEQ ID NO: 2, wherein amino acid residue 564 consists of any amino acid other than proline.

14. An isolated biologically active fragment of the HIF-1α polypeptide according to the amino acid sequence of SEQ ID NO: 2 wherein the active fragment contains amino acid residues from position 402 through 574 of SEQ ID NO: 2, wherein amino acid residue 402 consists of any amino acid other than Pro.

15. An isolated biologically active fragment of the HIF-1α polypeptide according to the amino acid sequence of SEQ ID NO: 2 wherein the active fragment contains amino acid residues from position 402 through 574 of SEQ ID NO: 2, wherein amino acid residue 564 consists of any amino acid other than Pro.

16. Isolated biologically active fragments of the HIF-1α polypeptide according to the amino acid sequence of SEQ ID NO: 2 wherein the active fragment contains amino acid residues from position 402 through 574 of SEQ ID NO: 2, wherein amino acid residue 574 consists of any amino acid other than Leu and amino acid residue 402 consists of any amino acid other than proline.

17. Isolated biologically active fragments of the HIF-1α polypeptide according to the amino acid sequence of SEQ ID NO: 2 wherein the active fragment contains amino acid residues from position 402 through 574 of SEQ ID NO: 2, wherein amino acid residue 574 consists of any amino acid other than Leu and amino acid residues 564 and 402 consist of any amino acid other than prolines.

* * * * *